US012579164B2

(12) United States Patent
Wilson et al.

(10) Patent No.: US 12,579,164 B2
(45) Date of Patent: Mar. 17, 2026

(54) SYNCING OBJECTS FOR MULTIDEVICE SYNCHRONIZATION

(71) Applicant: Apple Inc., Cupertino, CA (US)

(72) Inventors: David T. Wilson, Bethel, VT (US); Pratik Solanki, San Jose, CA (US); Vishani Kankariya, Cupertino, CA (US); Netra S. Kenkarey, Milpitas, CA (US); Maher S. Tantawy, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/732,217

(22) Filed: Jun. 3, 2024

(65) Prior Publication Data

US 2024/0403320 A1 Dec. 5, 2024

Related U.S. Application Data

(60) Provisional application No. 63/471,232, filed on Jun. 5, 2023.

(51) Int. Cl.
*G06F 16/27* (2019.01)
*G16H 10/60* (2018.01)

(52) U.S. Cl.
CPC ............. *G06F 16/27* (2019.01); *G16H 10/60* (2018.01)

(58) Field of Classification Search
CPC ................................ G06F 16/27; G16H 10/60
See application file for complete search history.

(56) References Cited

U.S. PATENT DOCUMENTS

| | | | | |
|---|---|---|---|---|
| 11,581,099 | B1 * | 2/2023 | Rufo | G16H 20/13 |
| 12,002,579 | B1 * | 6/2024 | Arkoff | G16H 40/20 |
| 12,216,439 | B2 * | 2/2025 | Tran | G16H 50/30 |
| 2014/0232558 | A1 * | 8/2014 | Park | A61B 5/1118 |
| | | | | 340/870.16 |
| 2016/0051191 | A1 * | 2/2016 | Miller | A61B 5/0205 |
| | | | | 600/300 |
| 2016/0378950 | A1 * | 12/2016 | Reiner | G16H 70/40 |
| | | | | 705/2 |

(Continued)

OTHER PUBLICATIONS

International Application No. PCT/US2024/032370 , International Search Report and Written Opinion, Mailed On Sep. 9, 2024, 13 pages.

*Primary Examiner* — Mark E Hershley
(74) *Attorney, Agent, or Firm* — Kilpatrick Townsend & Stockton LLP

(57) ABSTRACT

A first user device associated with a user profile can receive a health database associated with the user profile from a service provider configured to store the health database. The first user device can receive first health information associated with the user profile. The first user device can generate a first health sync object based on the first health information. The first health sync object can include a first sync identity that includes a first hardware identifier indicative of the first user device and a first database identifier indicative of the health database. The first user device can determine to transmit the first health sync object to the service provider based on the first user device having responsibility to transmit health sync objects with the first sync identity to the service provider. The first user device can transmit the first health sync object to the service provider.

20 Claims, 14 Drawing Sheets

(56) References Cited

U.S. PATENT DOCUMENTS

| | | | |
|---|---|---|---|
| 2017/0039324 A1* | 2/2017 | Francois | G16H 10/60 |
| 2017/0201611 A1* | 7/2017 | Donley | H04M 1/72412 |
| 2017/0262604 A1* | 9/2017 | Francois | G16H 10/60 |
| 2017/0337350 A1* | 11/2017 | Kim | G06F 3/04815 |
| 2018/0150599 A1* | 5/2018 | Valdes | G06F 16/904 |
| 2018/0358119 A1* | 12/2018 | Bhushan | G16H 40/63 |
| 2021/0169417 A1* | 6/2021 | Burton | A61B 5/4857 |
| 2022/0121884 A1* | 4/2022 | Zadeh | G06N 3/006 |
| 2022/0142535 A1* | 5/2022 | Burstein | A61B 5/02055 |
| 2022/0157143 A1* | 5/2022 | Panneer Selvam | G04G 9/007 |
| 2022/0230479 A1* | 7/2022 | Palaniappan | H04W 4/44 |
| 2023/0104450 A1* | 4/2023 | Garriga Calleja | G16H 50/20 |
| | | | 705/2 |
| 2023/0154611 A1* | 5/2023 | Palandurkar | G06T 7/0014 |
| | | | 705/2 |
| 2023/0197214 A1* | 6/2023 | Arkoff | G16H 10/60 |
| | | | 705/3 |
| 2023/0201518 A1* | 6/2023 | Ruttenberg | G16H 50/30 |
| | | | 600/27 |
| 2024/0005432 A1* | 1/2024 | Aman | G16H 50/80 |
| 2024/0403320 A1* | 12/2024 | Wilson | G16H 10/60 |

* cited by examiner

300

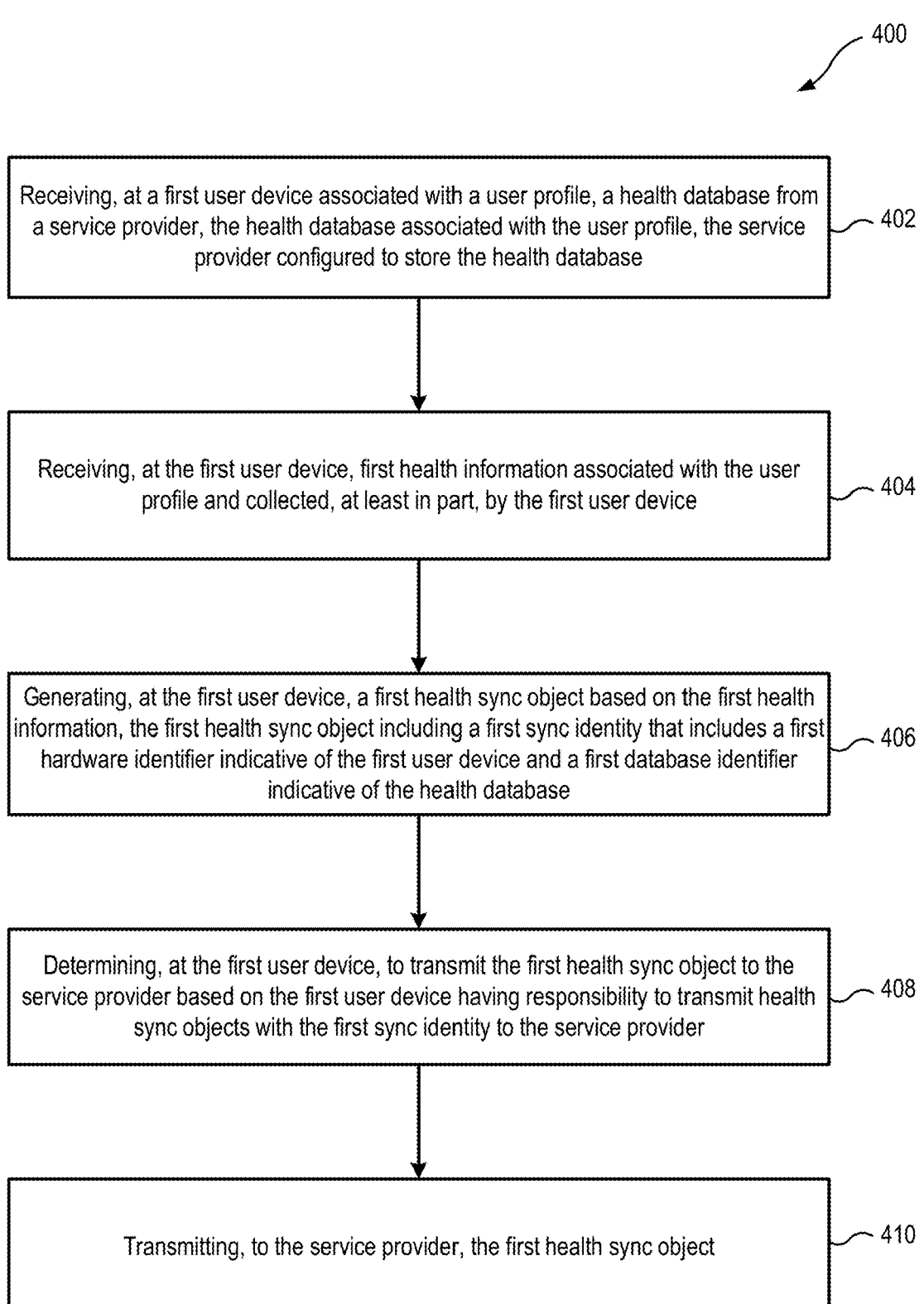

Receiving, at a first user device associated with a user profile, a health database from a service provider, the health database associated with the user profile, the service provider configured to store the health database ⟋ 402

Receiving, at the first user device, first health information associated with the user profile and collected, at least in part, by the first user device ⟋ 404

Generating, at the first user device, a first health sync object based on the first health information, the first health sync object including a first sync identity that includes a first hardware identifier indicative of the first user device and a first database identifier indicative of the health database ⟋ 406

Determining, at the first user device, to transmit the first health sync object to the service provider based on the first user device having responsibility to transmit health sync objects with the first sync identity to the service provider ⟋ 408

Transmitting, to the service provider, the first health sync object ⟋ 410

*FIG. 4*

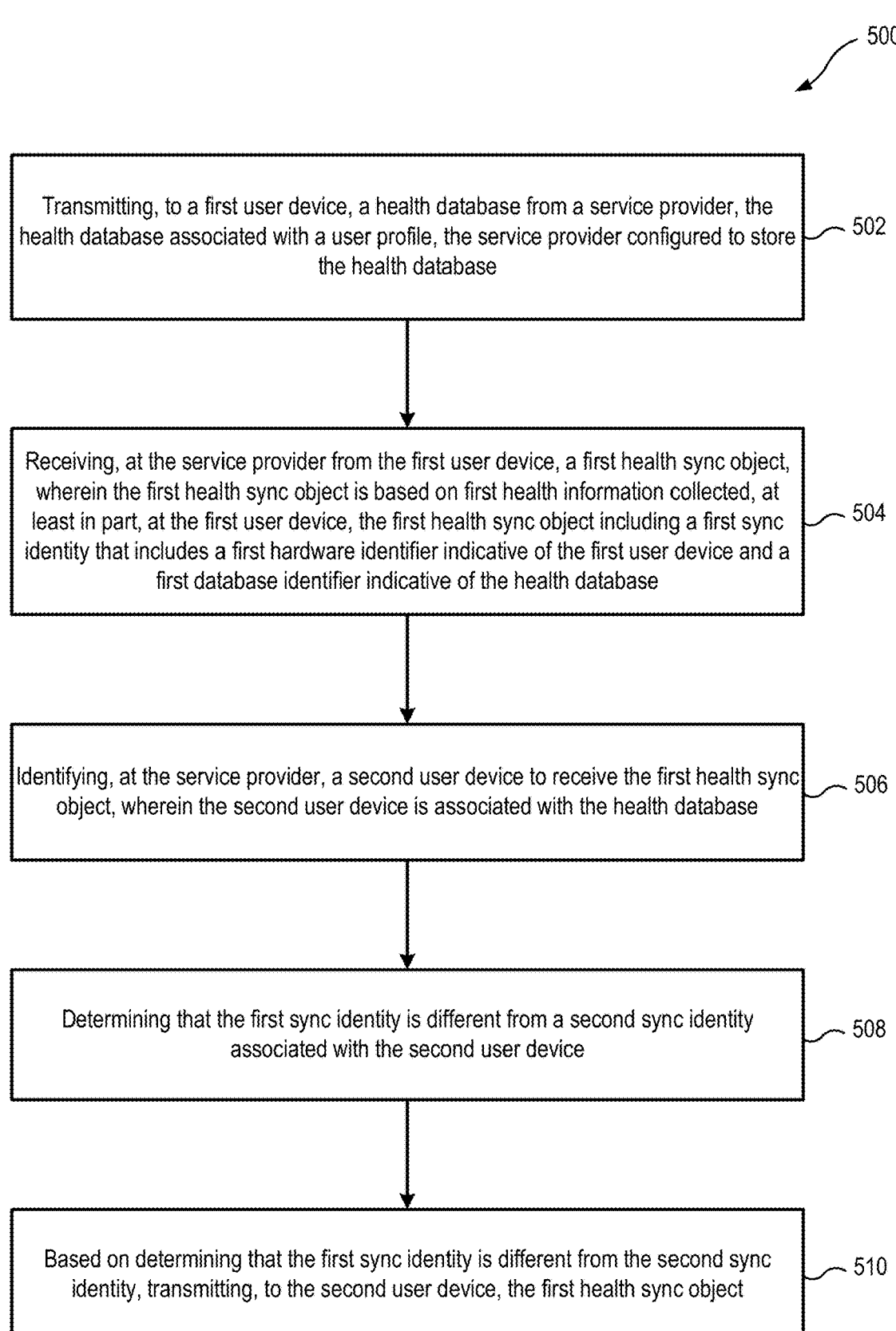

500

Transmitting, to a first user device, a health database from a service provider, the health database associated with a user profile, the service provider configured to store the health database
502

Receiving, at the service provider from the first user device, a first health sync object, wherein the first health sync object is based on first health information collected, at least in part, at the first user device, the first health sync object including a first sync identity that includes a first hardware identifier indicative of the first user device and a first database identifier indicative of the health database
504

Identifying, at the service provider, a second user device to receive the first health sync object, wherein the second user device is associated with the health database
506

Determining that the first sync identity is different from a second sync identity associated with the second user device
508

Based on determining that the first sync identity is different from the second sync identity, transmitting, to the second user device, the first health sync object
510

| Health Object | Sync Identity |
|---------------|---------------|
| A | L.X. <string> |
| B | L.Y. <string> |
| C | M.X. <string> |
| D | N.X. <string> |
| ... | ... |

616

| Health Object | Sync Identity |
|---------------|---------------|
| A | L.X. <string> |
| B | L.Y. <string> |
| C | M.X. <string> |
| D | N.X. <string> |
| ... | ... |

700

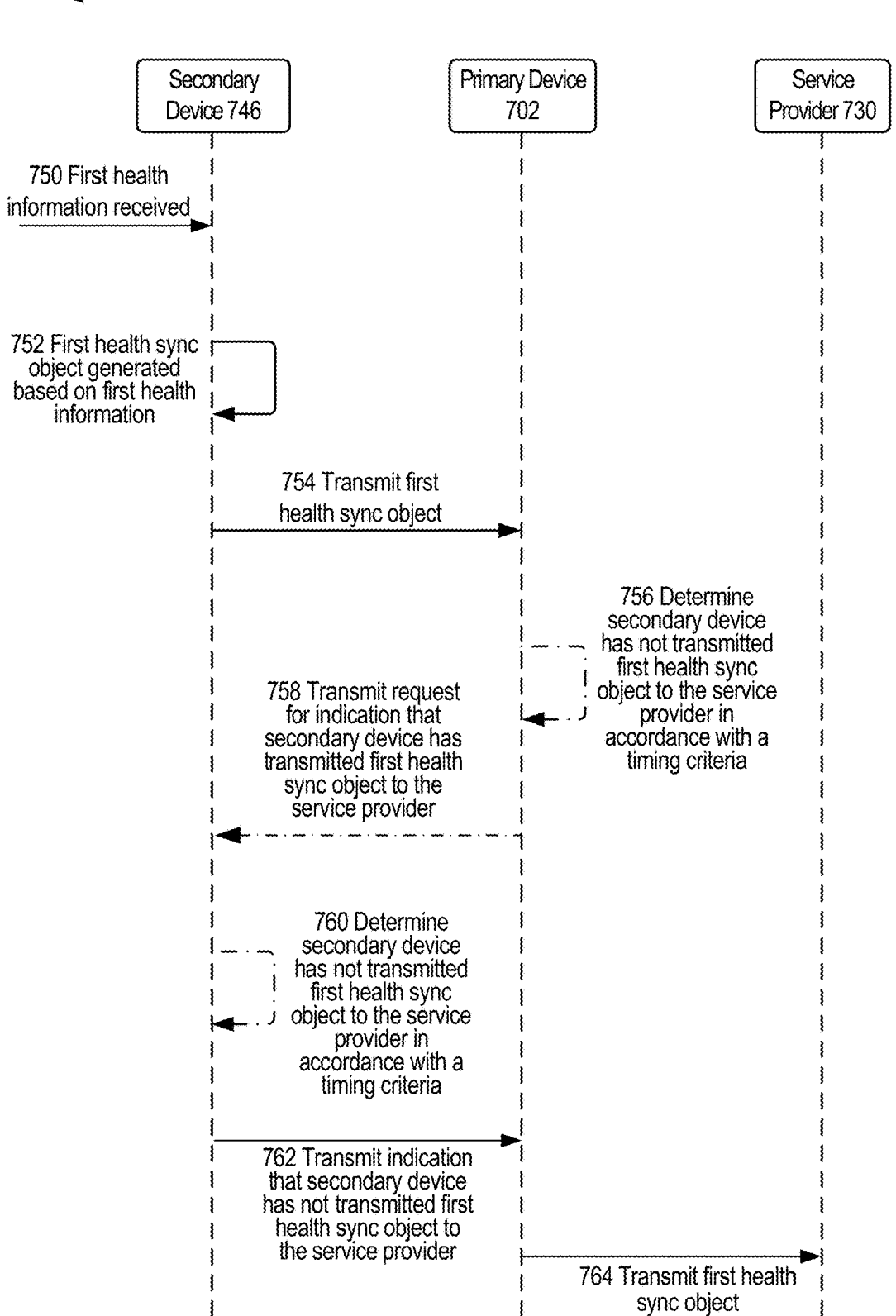

| Secondary Device 746 | Primary Device 702 | Service Provider 730 |

750 First health information received

752 First health sync object generated based on first health information

754 Transmit first health sync object

756 Determine secondary device has not transmitted first health sync object to the service provider in accordance with a timing criteria 758 Transmit request for indication that secondary device has transmitted first health sync object to the service provider 760 Determine secondary device has not transmitted first health sync object to the service provider in accordance with a timing criteria 762 Transmit indication that secondary device has not transmitted first health sync object to the service provider 764 Transmit first health sync object

*FIG. 7*

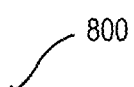

800

┌─────────────────────────────────────────────────────────────┐
│ Receiving, at a primary device, a first health sync object based on first health │
│ information associated with a user profile, the user profile associated with a health │
│ database, a service provider configured to store the health database, the first health │
│ sync object including a first sync identity, that includes a first hardware identifier │
│ indicative of the secondary device and a first database identifier indicative of the health │
│ database, the secondary device configured to transmit the first health sync object to the │
│ service provider │
└─────────────────────────────────────────────────────────────┘ 802

┌─────────────────────────────────────────────────────────────┐
│ Receiving, at the primary device, an indication that the secondary device has not │
│ transmitted the first health sync object to the service provider in accordance with a │
│ timing criteria │
└─────────────────────────────────────────────────────────────┘ 804

┌─────────────────────────────────────────────────────────────┐
│ Transmitting, to the service provider, the first health sync object │
└─────────────────────────────────────────────────────────────┘ 806

*FIG. 8*

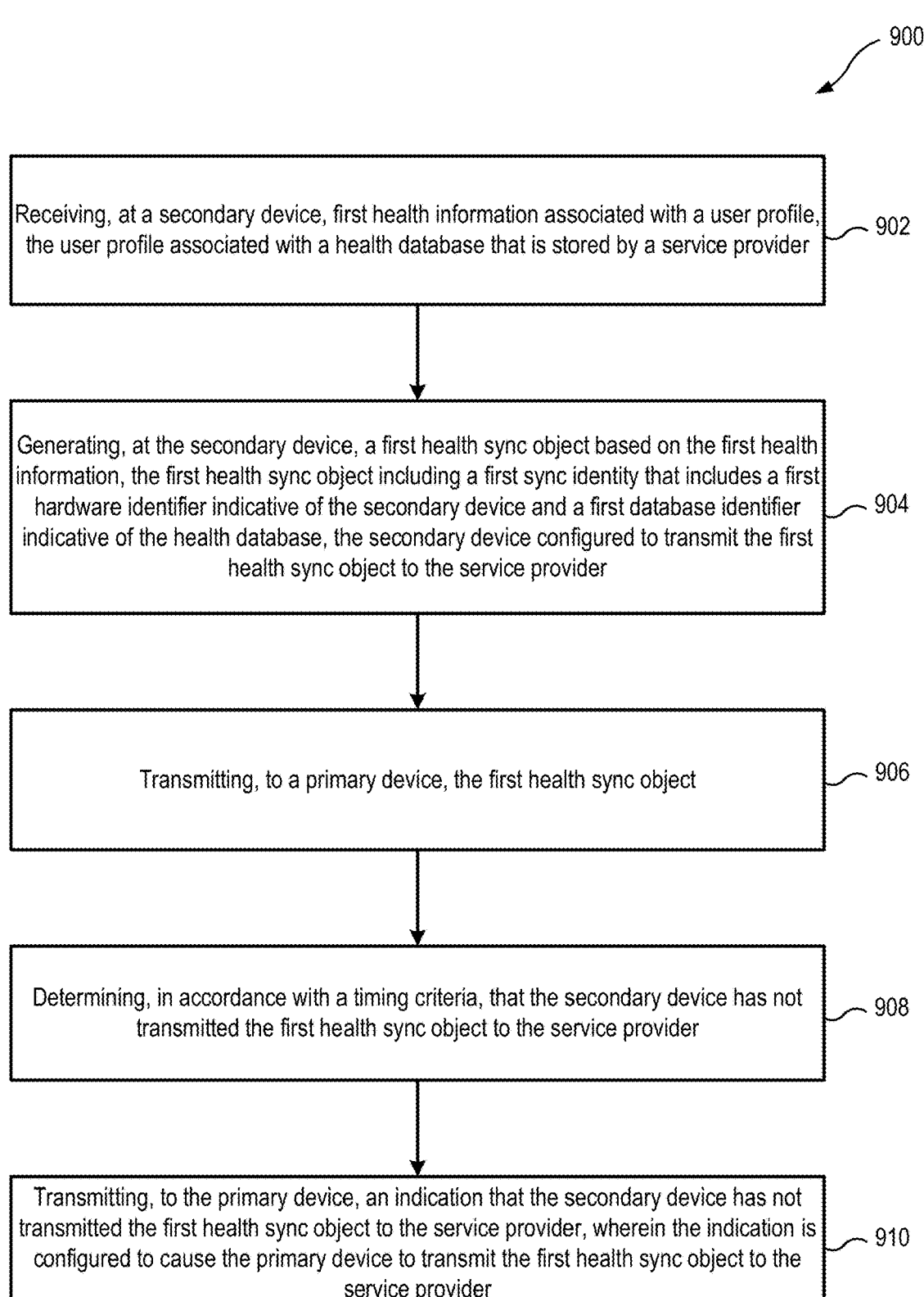

900

Receiving, at a secondary device, first health information associated with a user profile, the user profile associated with a health database that is stored by a service provider — 902

Generating, at the secondary device, a first health sync object based on the first health information, the first health sync object including a first sync identity that includes a first hardware identifier indicative of the secondary device and a first database identifier indicative of the health database, the secondary device configured to transmit the first health sync object to the service provider — 904

Transmitting, to a primary device, the first health sync object — 906

Determining, in accordance with a timing criteria, that the secondary device has not transmitted the first health sync object to the service provider — 908

Transmitting, to the primary device, an indication that the secondary device has not transmitted the first health sync object to the service provider, wherein the indication is configured to cause the primary device to transmit the first health sync object to the service provider — 910

1300
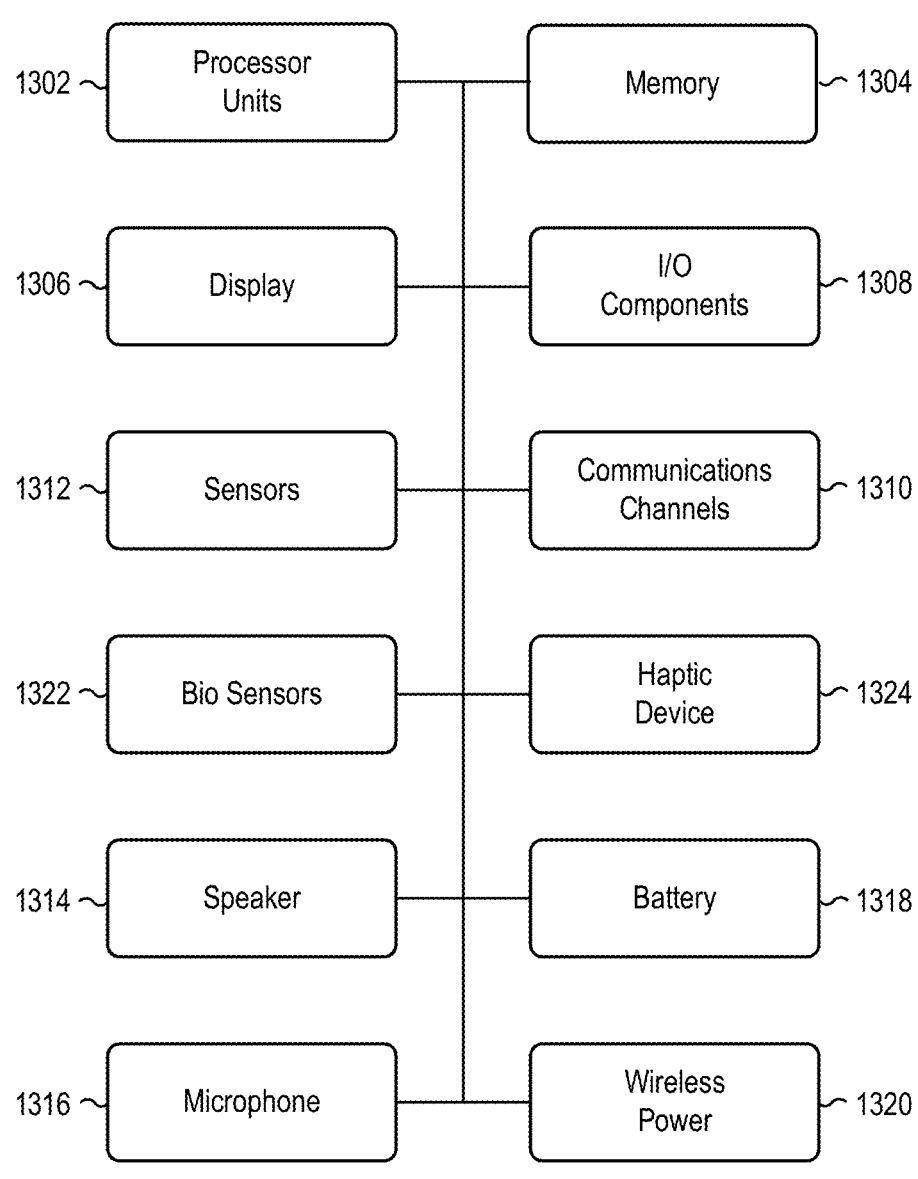
1302 — Processor Units
1304 — Memory
1306 — Display
1308 — I/O Components
1312 — Sensors
1310 — Communications Channels
1322 — Bio Sensors
1324 — Haptic Device
1314 — Speaker
1318 — Battery
1316 — Microphone
1320 — Wireless Power
*FIG. 13*

SYNCING OBJECTS FOR MULTIDEVICE SYNCHRONIZATION

CROSS-REFERENCES TO RELATED APPLICATIONS

This application claims priority under 35 U.S.C. § 119 (e) to U.S. Provisional Application Ser. No. 63/471,232, filed Jun. 5, 2023, entitled "MULTIDEVICE SYNCHRONIZATION OF HEALTH INFORMATION," which is incorporated herein by reference in its entirety.

BACKGROUND

Electronic devices, especially portable electronic user devices, are quickly becoming ubiquitous in every modern society. Such devices can be used to collect and store personal information, such as health data, about a user.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer-implemented method includes receiving, at a first user device associated with a user profile, a health database from a service provider. The health database can be associated with the user profile. The service provider can be configured to store the health database. The computer-implemented method also includes receiving, at the first user device, first health information associated with the user profile and collected, at least in part, by the first user device. The computer-implemented method also includes generating, at the first user device, a first health sync object based on the first health information. The first health sync object can include a first sync identity that includes a first hardware identifier indicative of the first user device and a first database identifier indicative of the health database. The computer-implemented method also includes determining, at the first user device, to transmit the first health sync object to the service provider based on the first user device having responsibility to transmit health sync objects with the first sync identity to the service provider. The computer-implemented method also includes transmitting, to the service provider, the first health sync object.

Another general aspect includes another computer-implemented method. The computer-implemented method includes transmitting, to a first user device, a health database from a service provider. The health database can be associated with a user profile. The service provider can be configured to store the health database. The computer-implemented method includes receiving, at the service provider from the first user device, a first health sync object. The first health sync object can be based on first health information collected, at least in part, at the first user device. The first health sync object can include a first sync identity that includes a first hardware identifier indicative of the first user device and a first database identifier indicative of the health database. The computer-implemented method includes identifying, at the service provider, a second user device to receive the first health sync object. The second user device can be associated with the health database. The computer-implemented method includes determining that the first sync identity is different from a second sync identity associated with the second user device. The computer-implemented method includes based on determining that the first sync identity is different from the second sync identity, transmitting, to the second user device, the first health sync object.

Another general aspect includes another computer-implemented method. The computer-implemented method includes receiving, at a primary device, a first health sync object based on first health information associated with a user profile. The user profile can be associated with a health database. A service provider can be configured to store the health database. The first health sync object can include a first sync identity, that includes a first hardware identifier indicative of the secondary device and a first database identifier indicative of the health database. The secondary device can be configured to transmit the first health sync object to the service provider. The computer-implemented method includes receiving, at the primary device, an indication that the secondary device has not transmitted the first health sync object to the service provider in accordance with a timing criteria. The computer-implemented method includes transmitting, to the service provider, the first health sync object.

Another general aspect includes another computer-implemented method. The computer-implemented method includes receiving, at a secondary device, first health information associated with a user profile. The user profile can be associated with a health database that is stored by a service provider. The computer-implemented method includes generating, at the secondary device, a first health sync object based on the first health information. The first health sync object can include a first sync identity that includes a first hardware identifier indicative of the secondary device and a first database identifier indicative of the health database. The secondary device can be configured to transmit the first health sync object to the service provider. The computer-implemented method includes transmitting, to a primary device, the first health sync object. The computer-implemented method includes determining, in accordance with a timing criteria, that the secondary device has not transmitted the first health sync object to the service provider. The computer-implemented method includes transmitting, to the primary device, an indication that the secondary device has not transmitted the first health sync object to the service provider. The indication can be configured to cause the primary device to transmit the first health sync object to the service provider.

DESCRIPTION OF THE DRAWINGS

FIG. 4 illustrates a flowchart of a process for synchronizing health information using sync identity across multiple devices, according to at least one example.

FIG. 5 illustrates a flowchart of a process for synchronizing health information using sync identity across multiple devices, according to at least one example.

FIG. 7 illustrates a flowchart of a process for synchronizing health information across primary and secondary devices, according to at least one example.

FIG. 8 illustrates a flowchart of a process for synchronizing health information across primary and secondary devices, according to at least one example.

FIG. 9 illustrates a flowchart of a process for synchronizing health information across primary and secondary devices, according to at least one example.

FIG. 13 illustrates a simplified block diagram including components of an example electronic device for implementing techniques relating to conducting sharing of health data updates among user devices and identifying changes in health data, according to at least one example.

DETAILED DESCRIPTION

Figure 1:
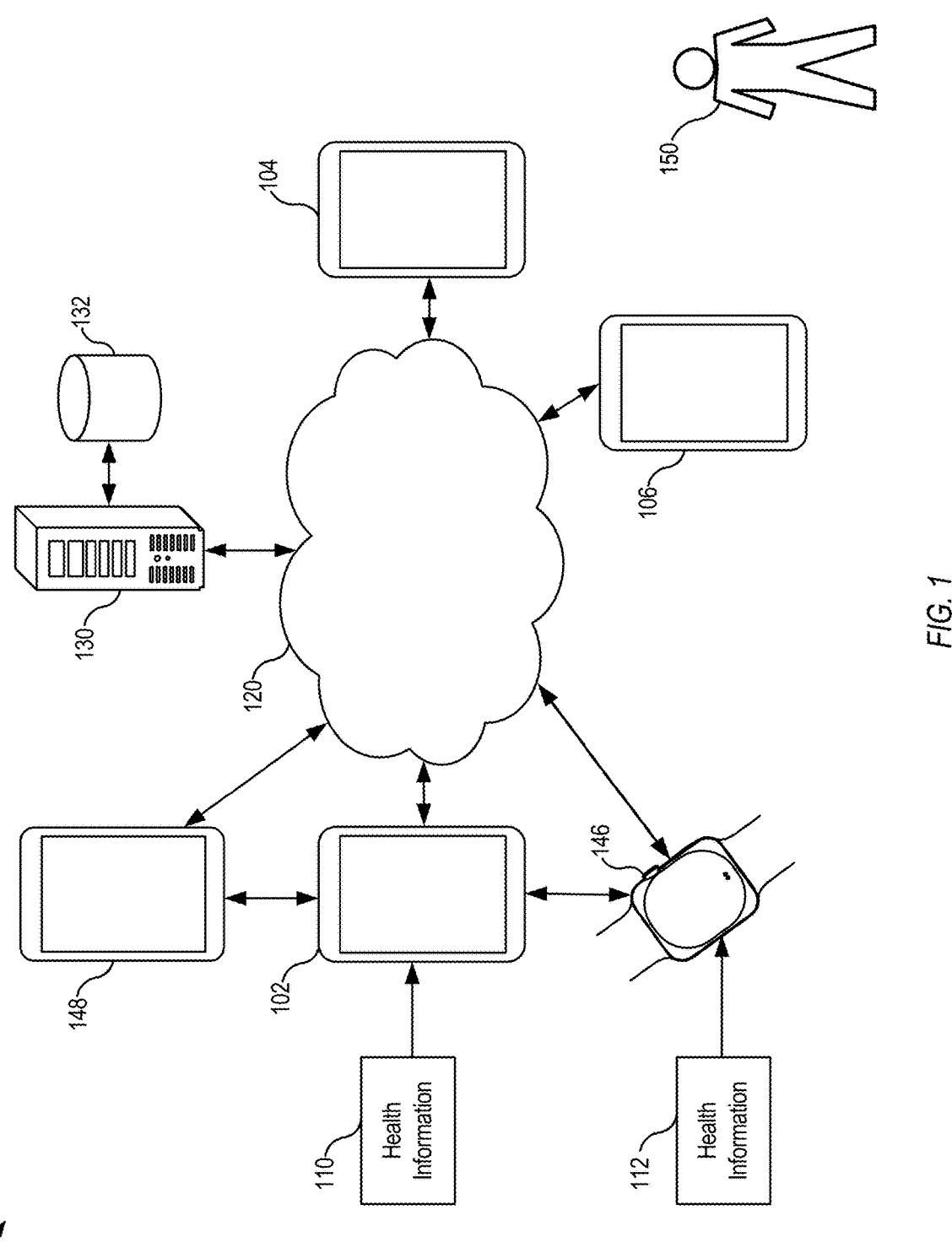
FIG. 1 illustrates a block diagram for synchronizing health information across multiple devices, according to at least one example.

Certain embodiments of the present disclosure relate to devices, computer-readable medium, and methods for implementing various techniques for various features of multidevice synchronization of health information. In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Examples of the present disclosure are directed to, among other things, methods, systems, devices, and computer-readable media that provide mechanisms for synchronizing health information across multiple devices. The techniques described herein enable synchronization of health information across multiple devices, including multiple types of devices, associated with a single profile (e.g., a single user account used on each of the multiple devices). Example devices can include phones, smartwatches, laptops, computers, computing devices, or any electronic user device.

In some conventional health information-sharing systems involving multiple devices, synchronization (also referred to as a sync or syncing) of the health information across multiple devices involves having a source of truth at a single device or service provider. Each device of the multidevice health information system can receive or generate health information and transmit the health information to the source of truth. When a device is transmitting health information to the source of truth, the synchronization operation can be referred to as an outgoing synchronization or outgoing sync. When a device is receiving health information from the source of truth, the synchronization operation can be referred to as an incoming synchronization or incoming sync.

The health information stored at the source of truth can be mirrored at each device. To enable a device to be a source of truth for all health information across multiple devices, the multidevice health information system may require robust, fast, bandwidth-intensive, and power-intensive information synchronization systems to makes sure the source of truth has the most up-to-date health information from all devices to mirror to the multiple devices. Such a multidevice health information system may require constant transmission of information from devices to the source of truth device/service provider which would be bandwidth and power intensive for all devices involved. Synchronization from the devices receiving/generating health information to the source of truth may require each particular device to transmit all health information at the particular device in order to verify that the source of truth has received all health information from the particular device. This may result in redundant transmission of health information already synchronized across the multiple devices to the source of truth device/service provider. Similarly, synchronization of health information to a device would require verifying that all health information from the source of truth is mirrored at each device. Thus, each synchronization operation to a particular device may require some sort of packaging or verification of all health information.

The techniques described herein enable each device, in a multidevice health information system, to optimize the outgoing sync of health information received or generated at the particular device to the source of truth. Likewise, the techniques described herein enable each device, in a multidevice health information system, to optimize the incoming sync of health information generated or synchronized at other devices from the source of truth. In this way, synchronization of health information across the multidevice health information system does not require constant mirroring and verification of all health information at each device. Here, whenever health information is received or generated at a particular device, the particular device adds an immutable sync identity to the health information. The sync identity is associated with the particular device and designates the particular device as responsible for outgoing synchronization of the health information. With the use of a sync identity, a particular device can determine which health information to include in an outgoing sync to the source of truth, such as the health information generated or received at the particular device. The particular device can partition health information into two groups: 1) health information for which the particular device is responsible to sync to the source of truth and 2) health information for which the particular device can trust that another device is responsible to sync to the source of truth. Similarly with the use of a sync identity, the source of truth can determine which health information to include in an incoming sync to a particular device, such as the health information generated or received at other devices in the multidevice health information system. The service provider can partition health information into two groups when transmitting health information to a user device: 1) health information to sync to not sync to the user device because the user device is responsible for that health information and thus already has the health information and 2) health information to sync to the user device because the user device is not responsible for that health information. Such techniques reduces the resources necessary to synchronize health information across the multiple devices at both the source of truth and at each device.

Turning now to a first particular example, a first user device (e.g., a smartphone) can perform an outgoing synchronization operation by synchronizing health information with a sync identity of the first user device to a source of truth (e.g., a service provider). This operation is considered an outgoing synchronization operation because the health information is outgoing to the service provider from the perspective of the first user device. The first user device can have a health database (which can also be referred to as a health information datastore or health datastore) that is synchronized to a health database of the service provider. The first user device can receive first health information associated with a user profile (also referred to as an account). For example, the first user device can receive information by a user inputting health information into the first user device or via sensors of the first user device. The first user device can generate a first health sync object (also referred to as a health information object) based on the first health information. A health sync object can represent a fundamental unit of health information that can be synchronized between the first user device, the source truth, and any other device in the multidevice health information system. When the first health sync object is generated by the first user device, the first health sync object includes an immutable sync identity associated with the first user device. The sync identity can include a hardware identifier indicative of the first user device. The sync identity can also include a first database identifier indicative of the health database associated with the user. In some examples, the first database identifier is indicative of a health database on the first user device. In some examples, the first database identifier is indicative of a health database of the service provider such that all user devices connected to the health database of the service provider would use the same first database identifier. When the first user device performs outgoing synchronization operation, the first user device identifies health sync objects (e.g., the first health sync object) with the sync identity of the first user device. The first user device can then sync these health sync objects to the source of truth. In some examples, the first user device has responsibility to perform outgoing synchronization operations for health sync objects with sync identities other than the first user device as described herein. For example, the first user device can be responsible for synchronizing health sync objects of a secondary device (e.g., a connected smartwatch) associated with the first user device or a user device that has been deactivated.

Turning now to a second particular example, a source of truth (e.g., a service provider) can perform an incoming synchronization operation to a first user device (e.g., a tablet) by synchronizing health information with a sync identity of a second user device (e.g., a smartphone) to the first user device. This operation is considered an incoming synchronization operation because the health information is incoming from the perspective of the first user device. The service provider can have a health database that is synchronized to the first user device and the second user device. The service provider can receive a second health sync object from the second user device, where the second health sync object was generated by the second user device after the second user device received second health information. The second health sync object can have an immutable second sync identity associated with the second user device. The second sync identity can include a hardware identifier indicative of the second user device. The second sync identity can also include a first database identifier indicative of the health database associated with the user. In some examples, the first database identifier is indicative of a health database of the service provider such that all user devices connected to the health database of the service provider would use the same first database identifier. In some examples, the second sync identity can include a second database identifier indicative of a health database on the second user device. The service provider can store information regarding which devices are associated with which sync identities. For example, the service provider can store information that the second user device is associated with the second sync identity. Likewise, the service provider is aware that the first user device is associated with a first sync identity. When the service provider receives the second health sync object, the service provider can identify that the first user device has a first sync identity and has not received the second health sync object. In some examples, the service provider can track health sync objects that have been received since the last incoming synchronization operation to the first user device. In some examples, the service provider includes some or all health sync objects with a sync identity other than the sync identity of the first user device when performing an incoming synchronization operation to the first user device. In some examples, the service provider is aware that the first user device has responsibility for multiple sync identities such that the service provider includes some or all health sync objects with a sync identity other than the sync identities under the responsibility of the first user device.

The techniques described herein also enable primary user devices (e.g., a smartphone) to perform outgoing synchronization operations and incoming synchronization operations with a source of truth (e.g., a service provider) on behalf of associated secondary user devices (e.g., a smartwatch). As described herein, a secondary user device can be a device with limited functionality that is paired with a primary user device. In one example, a primary device is a smartphone and the associated secondary device is a smartwatch. The smartwatch may have limited functionality compared to the smartphone because of hardware or software limitations. For example, the smartwatch may have limited memory, storage, bandwidth, network capability, battery, and/or processing power as compared to the smartphone. In another example, a primary device is a smartphone and a secondary device is a smartphone with comparatively limited functionality. Here, the smartphone with limited functionality may have limited functionality in the form of limited network capabilities, limited processing power, limited battery, or software limitations, or other limitations. The primary user device can be referred to as a parent device and the secondary user device can be referred to as a child device.

As described herein, the primary user device performs outgoing synchronization operations and incoming synchronization operations on behalf of an associated secondary user device to the service provider. In some examples, the primary user device can connect, transmit, and receive information from the secondary user device via a communication channel that is less resource intensive. For example, the primary user device and the secondary user device can communicate over a local area network (e.g., WiFi) or a short range communication medium (e.g. Bluetooth). This compares to a long range communication medium that may be more resource intensive such as a cellular network. In this example, the secondary user device generates health sync objects from health information received by the secondary user device and then transmits these health sync objects to the primary user device. After the expiration of a timing criteria (e.g., within a time period after the secondary user device has generated the health sync object), the secondary user device can determine that it has not transmitted its health sync objects to the service provider. The secondary user device can transmit an indication to the primary user device indicating that the primary user device should perform an outgoing synchronization operation for health sync objects generated by the secondary user device. In some examples, the primary user device can transmit a request to the secondary user device asking if the secondary user device has performed an outgoing synchronization operation for health sync objects generated by the secondary user device.

However, in some examples, the secondary user device can perform outgoing synchronization operations to the source of truth on its own behalf under certain conditions. For example, the secondary user device can use a local area network to communicate with a wide area network and by extension the source of truth.

Turning now to a third particular example, a primary user device (e.g., a smartphone) can perform an outgoing synchronization operation on health sync objects received from a secondary user device (e.g., a smartwatch) to a source of truth (e.g., a service provider). Here, the secondary user device received first health information and generated a first health sync object. For example, the smartwatch used sensors to detect a heart rate of a user. The secondary user device then generates the first health sync object based on the first health information. The first health sync object includes a first sync identity. The first sync identity may include a first hardware identifier associated with the secondary device and a database identifier associated with a database of health information associated with the user. The secondary user device transmits the first health sync object to the primary user device. In some examples, after a timing criteria expires, the secondary user device transmits an indication to the primary user device indicating that the primary user device should transmit the first help sync object to the service provider. In some examples, after a second timing criteria expires, the primary user device transmits a request to the secondary user device asking if the secondary user device has transmitted the first health sync object to the service provider. The secondary user device can respond indicating that the secondary user device has not transmitted the first health sync object to the service provider. Here, the primary user device can transmit the first health sync object to the service provider.

The techniques described herein also enable user devices (e.g., a smartphone) to perform outgoing and incoming synchronization operations to a source of truth (e.g., a service provider) through one or more synchronization methods. Different types of health information can be synchronized (either in an outgoing or an incoming operation) by different synchronization methods. Example types of health information can include streaming information, state information, and analysis information. In some examples, streaming information can be synchronized (also referred to as synced) via a changes sync method. In some examples, state information can be synced via a state sync method. In some examples, analysis information can be synced via a context sync method.

Streaming information can include information representing changes over time. For example, streaming information can include step tracking, calorie burning, medications taken over time, heart rate, and any other suitable data or information that changes over time. Streaming data can be considered unbounded because streaming data does not represent an absolute state of the information but rather the changes from a previous state. Health information from a user device that represents streaming information can be synced to the service provider and eventually other user devices via the changes sync method. The changes sync method can transmit the changes in the health information to the service provider via an outgoing synchronization operation. The changes sync method can also include the service provider transmitting the changes in health information to other user devices via an incoming synchronization operation. In this way, the changes sync method represents a stream of changes in health information that are periodically synchronized across the service provider and the user devices. To keep this type of streaming information synchronized across multiple devices via the changes sync method can be taxing on bandwidth consumption, network resources, computing/processing power, and battery life of the user devices when used for all types of health information. As such the changes sync method may only be used for important health information or health information that may be best represented as a log of changes. Example health information that may be best represented as a log of changes includes step tracking, calorie burning, heart rate, etc. However, the changes sync method may not be optimal when a device has limited resources for bandwidth, network, computing/processing power, and/or battery life. For example, synchronizing health information via the changes sync method to a smartwatch may be too demanding on the smartwatch's resources such as bandwidth, network, and battery life.

Another type of health information can be state information. State information represents a bounded piece of information that represents the actual state of the information. State information is different than streaming information which is meant to convey the changes that have occurred. In some examples, state information is bounded to a time window such that the state information represents the actual state during that time window. For example, a current list of medications a user uses can be stored as state information because the current list of medications represents an actual state of the list of medications. An example of streaming information related to a list of medications could be the changes in the dosage of medication or changes in the medication over time. Other examples of state information can include a list of diseases, ailments, and conditions of a user at a particular time.

State information can be synchronized between the user devices (e.g., a smartphone, smartwatch, tablet, laptop, etc.) and a source of truth (e.g., a service provider) via a state sync method. The state sync method can be used to sync state information across the multidevice health information system. The state sync method enables user devices and the service provider to transmit the actual state of health information rather than the changes in health information over time (for example, streaming information described herein). The state sync method may provide a high-level of consistency and accuracy for health information represented as state information across the multiple user devices because each user device can know that the state information represents actual health information rather than a stream of changes to health information as seen with streaming information. The state sync method also can reduce the resources needed at the user devices and service provider to synchronize health information by reducing the need to constantly transmit and receive changes to health information. In some examples, streaming information can be bounded into state information. In one example a user's medication history is a stream of medication names and doses taken which represents streaming information. The stream of doses taken can be bounded into a window of the history of the stream of doses taken during a specific time window. By bounding the stream of doses take in into a window the dose history becomes a state that can be synchronized via the state sync method.

Synchronizing health information via the state sync method can be less resource intensive than the change sync method. For example, the change sync method can involve sending a stream of changes to the health information over time in order to make the health information eventually consistent across multiple devices. In one example, tracking medications taken through change sync can include an update for each time a medication was taken. This type of synchronization can be demanding on bandwidth, network, computing/processing power, and/or battery life at the user devices and/or the service provider. Alternatively, tracking medication taken as a state represents a state of the medications taken at a specific time or during a specific window. State synchronization can be consistent across the multidevice health information system relatively quickly because the synchronization of the health information represents a picture of the health information at a specific time rather than a best effort delivery of changes to the health information over time.

Another type of health information can be stored both at the user devices and at the service provider as analysis information. Analysis information includes observations, suggestions, diagnoses, algorithms, predictions based on raw health information, and any other suitable information that can be used as analysis. For example, diagnosing a person to have a disease or condition based on symptoms is an example of analysis information. Analysis information is highly dependent on the algorithms and/or processing of raw health information. Raw health information can include symptoms, heart rate, temperature, blood oxygen, etc. However, algorithms for different health applications can change as the version of the application changes. The algorithm can also be different based on the computing and/or other resources on the user device or can change due to updates in science/understanding. In order to synchronize analysis information across multiple devices with potentially different algorithms, the applicable health information can be synchronized through a context sync method.

Analysis information can be synchronized between the user devices (e.g., a smartphone, smartwatch, tablet, laptop, etc.) and a source of truth (e.g., a service provider) via a context sync method. One way in which the context sync method can be used is to sync analysis information across the multidevice health information system. The context sync method can be used to create consistent analysis information from the multidevice health information system by merging analysis information from multiple user devices which may have generated different analysis information based on each user devices' algorithms.

In order to generate consistent analysis information, the service provider needs to understand the context of each user device. The service provider can store device information regarding each user device. For example, the service provider can store the type of user device such as whether a user device is a smartphone, smartwatch, laptop, tablet, etc. By storing device information, a more intelligent synchronization of the health information can be enabled. A more intelligent synchronization of the health information can reduce power consumption needs when synchronizing the health information across multiple devices. Each device can see a reduction in power consumption for synchronization of the health information.

The service provider can receive the device information when the user device is setup to connect to the multidevice health information system. When a user device first enables synchronization of health data to the service provider through an account, the user device (or software on the user device) can create a device context record and send the device context record to the service provider. The device context record can include device information such as a device unique identifier and/or a device type. The device context records can be stored in a database table at the service provider.

Other device specific information can also be useful for the service provider and/or user devices of the multidevice health information system. For example, the service provider can also store device-specific key value data that can be useful for software and applications on user devices. Example key value data can include other device specific information such as an operating system version for the operating system on the device and/or an application version for the application on the device. User devices and/or the service provider can query the service provider for the device-specific key value data of user devices in the multidevice health information system.

Software and/or applications on the user devices and service provider can use the device context record and the device-specific key value data when determining how to merge health information (for example, analysis information) across a user's health information account such that the health information at the health information databases on the user devices and at the service provider are merged. User devices are able to query the key value data of other devices and the device context records of other devices for synchronization operations.

The context sync method can also be used in tandem with other synchronization methods in order to determine the best times and/or circumstances to synchronize health information to particular user devices. For example, the service provider can use device information to determine that a particular user device is a smartwatch with limited resources. The service provider can determine when not to synchronize health information to a particular user device and/or when to synchronize health information to a particular user device based on information about the particular user device.

The examples described herein address a number of technical problems and provide for a number of technical improvements. In some examples, these improvements additionally improve the functioning of various components of a system in which the techniques are implemented. The techniques described herein provide for synchronization of health information that minimizes network traffic and minimizes power consumption of user devices, as compared to conventional systems. For example, the techniques described herein enable each user device (e.g., a smartphone, smartwatch, laptop, etc.) in a multidevice health information system to optimize the outgoing sync of health information to focus on health information received or generated at the particular user device to a source of truth (e.g., a service provider). Likewise, the techniques described herein enable each device in a multidevice health information system to optimize the incoming sync of health information to focus on health information generated or synchronized at other devices. The techniques described herein also enable synchronizing of new types of health information such as state health information and analysis information, while also minimizing the resource consumption for synchronization of health information across the multidevice health information system by using a state sync method and a context sync method in addition to a change sync method.

Additionally, the techniques described herein also enable primary user devices (e.g., a smartphone) to perform outgoing synchronization operations and incoming synchronization operations with a source of truth (e.g., a service provider) on behalf of associated secondary user devices (e.g., a smartwatch) when the secondary user device is unable to perform synchronization operations due to limited functionality such as limited network capabilities, limited processing power, limited battery, or software limitations, or other limitations. This enables the multidevice health information system to include user devices that have limited functionality while maintaining consistency of health information across the multidevice health information system. Likewise, enabling user devices that have limited functionality to be a part of the multidevice health information system enables the multidevice health information system to receive and analyze information from more devices and thus provide better health information services to users.

For example, rather than sending notifications to display between devices, each device generates their own notifications based on the health information on each respective device. In a system where notifications are constantly sent between devices, devices would constantly be sending messages over the networks and consuming power to constantly send and receive notifications. By minimizing the sending of notifications and other messages between devices, devices can reduce network traffic, bandwidth usage, and increase battery life.

Turning now to the figures, FIG. 1 illustrates a block diagram for synchronizing health information across multiple devices, according to at least one example. The multidevice health information system can include a user device 102 that stores health information associated with an account of a user 150. Health information can include steps taken, calories burned, caloric/food intake, menstrual cycle tracking, medication tracking, health-related recommendations/suggestions, insights regarding the user's health, indications of trends in health data, the user's personal health record (e.g., medical record, dental record, etc.), and/or any other kind of health information. The health information on the user device 102 can be synced to an account (for example, a health information account) associated with the user 150 through a service provider 130. User devices 102, 104, 106, 146, 148 can communicate with the service provider 130 through a network 120. The network 120 can be any kind of network. For example, the network 120 can be a local area network (LAN) or a wide area network (WAN). The network 120 can be a WiFi network or an equivalent network. The network can be a Bluetooth network or other short-range network connecting only two devices. The network can be a proprietary communication channel between two devices, for example, a communication channel between a phone and a smartwatch.

The account can be accessed through communication with the service provider 130. The health information associated with the account can be stored in a health information database 132. The service provider 130 can communicate with the health information database 132 and sync health information between the user devices 102, 104, 106, 146, 148 (e.g., each of which may include its own health information datastore for storing health information) and the health information database 132. When the user device 102 receives new health information 110, the user device 102 may sync the new health information 110 with the service provider 130. As illustrated, the user can also have other user devices 104, 106, 146, 148 that share the same account. As such, each of these other user devices 104, 106, 146, 148 may also have access to the health information 110 of the user. Each user device can have its own health information datastore associated with the user. User devices 102, 104, 106 are illustrated as handheld portable user devices such as smartphones. As described herein, an example user device can be any suitable user device such as a smartphone, tablet, media player, laptop, wearable device, smartwatch, and the like. In some examples, the user device may include one or more applications, which may include custom-built algorithms and other logic, to enable performance of at least some of the techniques described herein. The user device can also include storage media for storing computer-executable instructions (e.g., that make up the application) and other data such as described herein. In some examples, the user devices 102, 104, 106, 146, 148 can be associated with a single user 150. In some examples, the user devices 102, 104, 106, 146, 148 can be associated with different users, but can all have access to the health information database 132 containing health information associated with the user 150.

The user device 102 can also be referred to as primary user device 102. Primary user device 102 can serve as a primary user device associated with user devices 146, 148. The user devices 146, 148 can also be referred to as secondary user devices 146, 148. The secondary user devices 146, 148 can also receive health information in the same ways as primary user devices, including primary user device 102, can receive health information as described herein. For example, the secondary user device 146 receives health information 112. As described herein, secondary user devices 146, 148 can be devices with limited functionality that is paired with the primary user device 102. In one example, the primary device 102 is a smartphone and the secondary device 146 is a smartwatch. The secondary user device 146 may have limited functionality compared to the primary user device 102 because of hardware or software limitations.

For example, the secondary user device 146 may have limited memory, storage, bandwidth, network capability, battery, and/or processing power as compared to the primary user device 102. In another example, a primary device 102 is a smartphone and a secondary device 148 is a smartphone with comparatively limited functionality. Here, the secondary user device 148 may have limited functionality in the form of limited network capabilities, limited processing power, limited battery, or software limitations, or other limitations. The primary user device 102 can be referred to as a parent device and the secondary user devices 146, 148 can be referred to as a child device.

Figure 2:
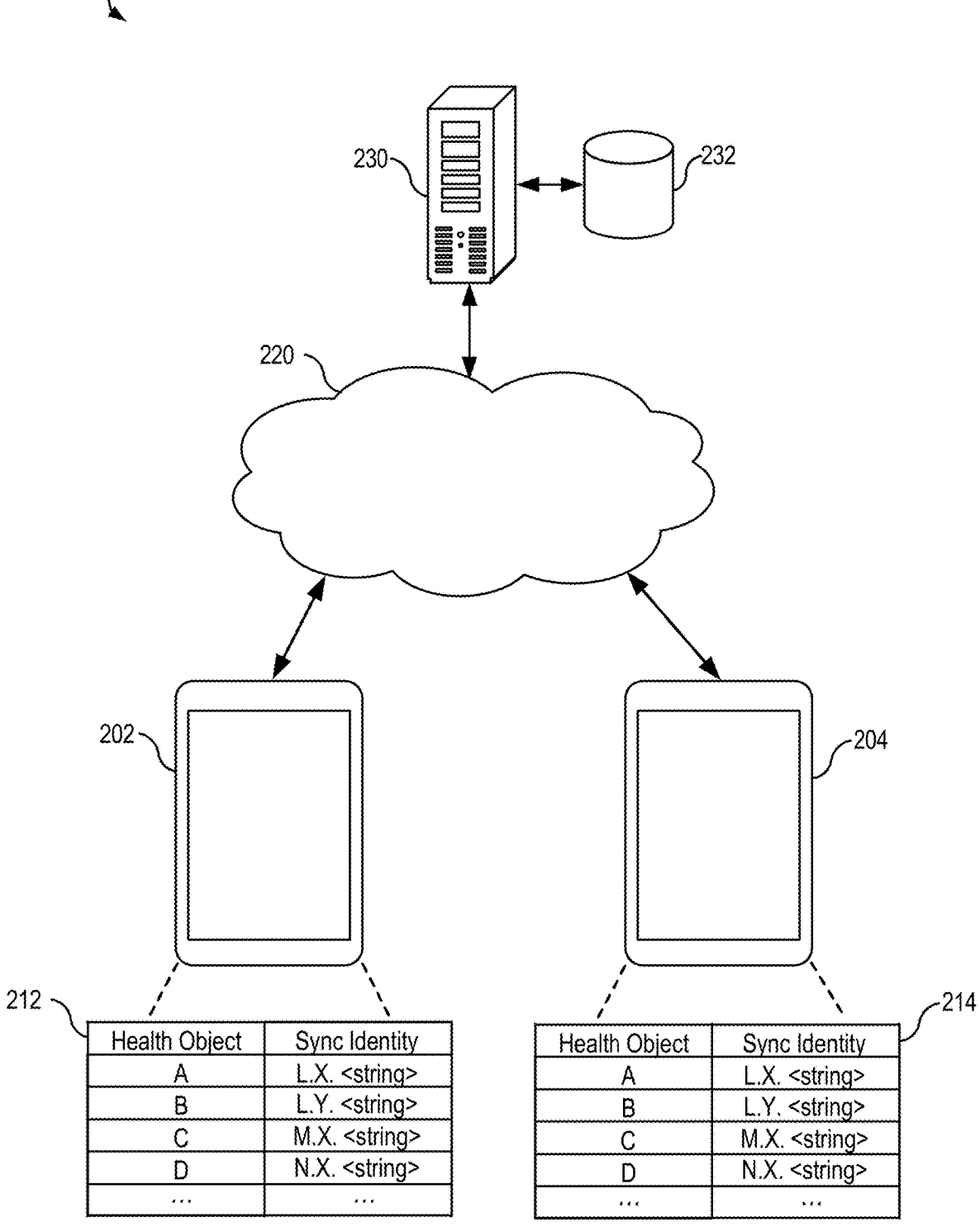
FIG. 2 illustrates a block diagram for synchronizing health information using a sync identity across multiple devices, according to at least one example.

FIG. 2 illustrates a block diagram 200 for synchronizing health information using a sync identity across multiple devices, according to at least one example. The multidevice health information system can include a user device 202 (for example, user device 102 of FIG. 1) that stores health information (for example, health information 110 of FIG. 1) associated with an account of a user (for example, the user 150 of FIG. 1). Health information can include steps taken, calories burned, caloric/food intake, menstrual cycle tracking, medication tracking, health-related recommendations/suggestions, insights regarding the user's health, indications of trends in health data, or any other kind of health information. The health information on the user device 202 can be synced to an account (for example, a health information account) associated with the user through a service provider 230 (for example, the service provider 130 of FIG. 1). User devices 202, 204 can communicate with the service provider 230 through a network 220 (for example, the network 120 of FIG. 1). The network 220 can be any kind of network. For example, the network 220 can be a local area network (LAN) or a wide area network (WAN). The network 220 can be a WiFi network or an equivalent network. The network can be a Bluetooth network or other short-range network connecting only two devices. The network can be a proprietary communication channel between two devices, for example, a communication channel between a phone and a smartwatch.

The account can be accessed through communication with the service provider 230. The health information associated with the account can be stored in a health information database 232 (for example, the health information database 132 of FIG. 1). The service provider 230 can communicate with the health information database 232 and sync health information between the user devices 202, 204 and the health information database 232. The user can also have other user devices, such as user device 204, that share the same account. As such, the other user device 204 may also have access to the health information of the user. Each user device can have its own health information datastore associated with the user. User devices 202, 204 are illustrated as handheld portable user devices such as smartphones. In some examples, the user devices 202, 204 can be associated with a single user. In some examples, the user devices 202, 204 can be associated with different users, but can all have access to the health information database 232 containing health information associated with the user.

The user device 202 can have a health information datastore 212. The health information data store can include health sync objects. When the user device 202 receives new health information, the user device 202 can generate a health sync object based on the new health information. In some examples, the health information can be received by the user device 202 via a user inputting the health information into the user device 202. In some examples, the health information can be obtained via sensors of the user device 202. In some examples, the health information can be collected from a web server. In some examples, the health information can be obtained from a server accessible through a network such as database from a medical provider. In some examples, the health information can be obtained from a gateway for a health database system. In some examples, the health information can be received from another user device which received health information. For example, the other user device can be a secondary device or an accessory device such as a smartwatch. In some examples, the another user device can receive health information via user input or via sensors of the another user device.

The health sync object can include the new health information and/or can include analysis information based on the new health information. In some examples, the new health information can be raw health information including symptoms, heart rate, temperature, blood oxygen, etc. Analysis information can include observations, suggestions, diagnoses, algorithms, predictions based on raw health information, and any other suitable information that can be used as analysis. For example, diagnosing a person to have a disease or condition based on symptoms is an example of analysis information.

When generating the health sync object, the user device 202 includes a sync identity with the health sync object. The sync identity can be used to aid the user device 202 (and other user devices in the multidevice health information system) to partition health information into two groups: 1) health information for which the user device 202 is responsible to sync to the service provider 230 and 2) health information for which the user device 202 can trust that another device (for example, user device 204) is responsible to sync to the service provider 230. The sync identity can be a tuple of two or three fields including two unique identifiers and an optional string. The two unique identifiers of a sync identity can be a hardware identifier and a database identifier, and the string can be an optional instance discriminator. The hardware identifier can be tied to the specific piece of hardware that generated the health sync object. For example, for a health sync object generated on user device 202, the hardware identifier would be indicative of the user device 202. Similarly, if the database on user device 202 is moved to another device, a new sync identity would be formed as a different piece of hardware would have a different hardware identifier. The database identifier can be tied to the specific database to which the health sync object relates. For example, the health sync object can be associated with a first user and the associated health information database associated with the first user. In some examples, a user device 202 can have access to multiple health information databases, for example, a health information database for the owner of the user device 202 and a health information database for a relative (such as a child, parent, or other family member). In some examples, a user device 202 can have access to multiple health information databases which may have access to different information about the same user. Each of these health information databases would be associated with different database identifiers. In some examples, the first database identifier is indicative of a health database on the user device 202 rather than a health information database associated with a first user across multiple devices. As noted previously, the user device 202 may have multiple health information databases that each have individual database identifiers. The optional instance discriminator can be a string that can be used to differentiate sync identities that might have the same hardware identifier and the same database identifier. For example, a new sync identity can be generated in cases where the hardware identifier and the database identifier have not changed.

In an example related to FIG. 2, the user device 202 has a health information datastore 212 including health sync objects (also referred to as health objects) with associated sync identities depicted as a table. In one example, health object A has a sync identity of L.X.<string>. L is indicative of a hardware identifier associated with the user device 202, which indicates that health object A was generated on user device 202. X is indicative of a database identifier associated with the owner of the user device 202, which indicates that the health object A includes health information for a health information database associated with the owner of the user device. <string> is indicative of the instance discriminator. In another example, health object B has a sync identity of L.Y.<string>. Health object B has the same hardware identifier L as health object A, which indicates that the user device 202 generated both health object A and health object B. However, health object B has a different database identifier Y than health object A. This indicates that health object B is associated with a different database than health object A. In one example, health object B can be associated with a database for a relative (such as a child, parent, or other family member) of the owner of user device 202. In another example, health object B can be associated with a second health information database associated with the owner of device 202. A user can be associated with multiple health information databases for a variety of reasons. In some examples, a user device can have multiple health information datastore that correspond to different database identifiers.

In another example, health object C has a sync identity of M.X.<string>. Health object C has a hardware identifier M which is different from the hardware identifier L of health object A. This indicates that the health object C was generated by a different device than user device 202, for example user device 204 can be the device that generated health object C. Health object C can have the same database identifier as health object A, indicating that health object C relates to the same database as health object A.

The user device 202 can use the sync identity of health sync objects to determine which health sync objects to sync to the service provider 230 during an outgoing synchronization operation. The user device 202 can sync health sync objects with the associated sync identity of the user device 202 to the service provider 230. In some examples, the user device 202 can sync health objects with the hardware identifier of the user device 202. For example, with reference to the example of health objects A and B above, the user device 202 can sync health sync objects with sync identity L.X and L.Y to the service provider 230 because the user device 202 is associated with the hardware identifier L. In some examples, the user device 202 can be authorized to only sync health sync objects associated with specific health information databases. For example, with reference to the example of health objects A and B above, the user device 202 can sync health sync object with sync identity L.X to the service provider 230 because the user device 202 is associated with the database identifier X and authorized to sync objects with a database identifier X. On the other hand, the user device 202 can be associated with database identifier Y and not be authorized to sync objects with database identifier Y. As such, the user device 202 does not sync health object B to the service provider 230.

The user device 202 can also have responsibility to sync health sync objects with other sync identities to the service provider. The user device 202 can have responsibility to sync health sync objects with hardware identifiers for deactivated or migrated devices. A deactivated device can be a device that is no longer active, no longer connected to a particular health information database, or a device that is no longer associated with the user. For example, when a user upgrades from an old smartphone to a new smartphone, the old smartphone would be deactivated and/or no longer active. The new smartphone can be responsible to sync health sync objects with a hardware identifier associated with the old smartphone. Alternatively, a migrated device refers to a device that migrated its information to a new device. For example, when a user decides to get a new smartphone and give their old smartphone to a relative (such as a child), the health information on the old smartphone can be migrated to the new smartphone. In this way, the old smartphone can be considered a migrated device. In some examples, when the health sync objects become the responsibility of the user device 202, the old sync identity can be replaced with the sync identity of the user device 202.

In an example related to FIG. 2, health object D has a sync identity of N.X.<string>. Health object D has a hardware identifier N which is different from the hardware identifier L of health object A. This indicates that the health object D was generated by a different device (not pictured in FIG. 2) than user device 202. Here, the device that generated health object D can be a deactivated device or a migrated device, meaning the device is no longer active or no longer connected to the health information database X. Here, the user device 202 can have responsibility for syncing health objects with a hardware identifier N to the service provider 230. As such, the user device 202 has responsibility for syncing health objects with a hardware identifier L and health objects with a hardware identifier N.

In this way, outgoing synchronization operations can be limited to health objects with sync identities associated with the user device performing the outgoing synchronization operation. This can limit redundant transmissions of health information within the multidevice health information system and thus limited the use of resources of the service provider 230 and the user devices 202, 204. Such resources can include bandwidth, network, computing/processing power, and/or battery life of the service provider 230 and/or the user device 202, 204. In this way, the user device can trust that another user device has responsibility for health sync object not generated by the user device.

In some examples, a sync identity tied to a specific device can be moved to be tied to another device in the multidevice information system. When a sync identity is moved from the specific device to another device, the specific device can generate a new sync identity. For example, user device 202 may have a sync identity M.X that is moved to user device 204. In some examples, the sync identity M.X is moved to the user device 204 purposefully by a user, or it can be moved by a bad actor. The user device 202 can detect that the sync identity M.X has moved to another device (the user device 202 may not be able to detect to which device sync identity M.X. has moved), and generate a new sync identity Q.X where a new hardware identifier Q is used instead of M. Here, user device 202 may still use the database identifier X because the user device 202 still has access to a health database shared among multiple devices and uses the appropriate database identifier X. In other examples, the user device 202 can generate a new sync identity Q.U where the database identifier U is indicative of a new health database being stored on the user device 202.

Similarly, the service provider 230 can use the sync identity of health sync objects to determine which health sync objects to sync to user devices during an outgoing synchronization operation. The service provider 230 can partition health information into two groups when transmitting health information to a user device (for example, user device 202): 1) health information to sync to not sync to the user device because the user device is responsible for that health information and thus already has the health information and 2) health information to sync to the user device because the user device is not responsible for that health information. During an outgoing synchronization operation to user device 202, the service provider 230 can sync health sync objects with sync identities not associated with user device 202. For example, with reference to the example of health objects A, B, C, and D above, the service provider 230 can sync health sync objects with sync identity M.X to the user device 202 because the user device 202 is not associated with the hardware identifier M (the user device 202 is associated with hardware identifier L and N). Likewise, during an outgoing synchronization operation to user device 204, the service provider 230 can sync health sync objects with sync identities not associated with user device 204. For example, with reference to the example of health objects A, B, C, and D above, the service provider 230 can sync health sync objects with sync identity L.X and N.X (and potentially L.Y) to the user device 204 because the user device 204 is not associated with the hardware identifier L and N (the user device 202 is associated with hardware identifier M).

In this way, incoming synchronization operations can be limited to health objects with sync identities not associated with the user device receiving the incoming synchronization operation. This can limit redundant transmissions of health information within the multidevice health information system and thus limited the use of resources of the service provider 230 and the user devices 202, 204. Such resources can include bandwidth, network, computing/processing power, and/or battery life of the service provider 230 and/or the user device 202, 204.

FIGS. 3-5, 7-9 illustrate example flow diagrams showing processes 300, 400, 500, 700, 800, and 900, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Figure 3:
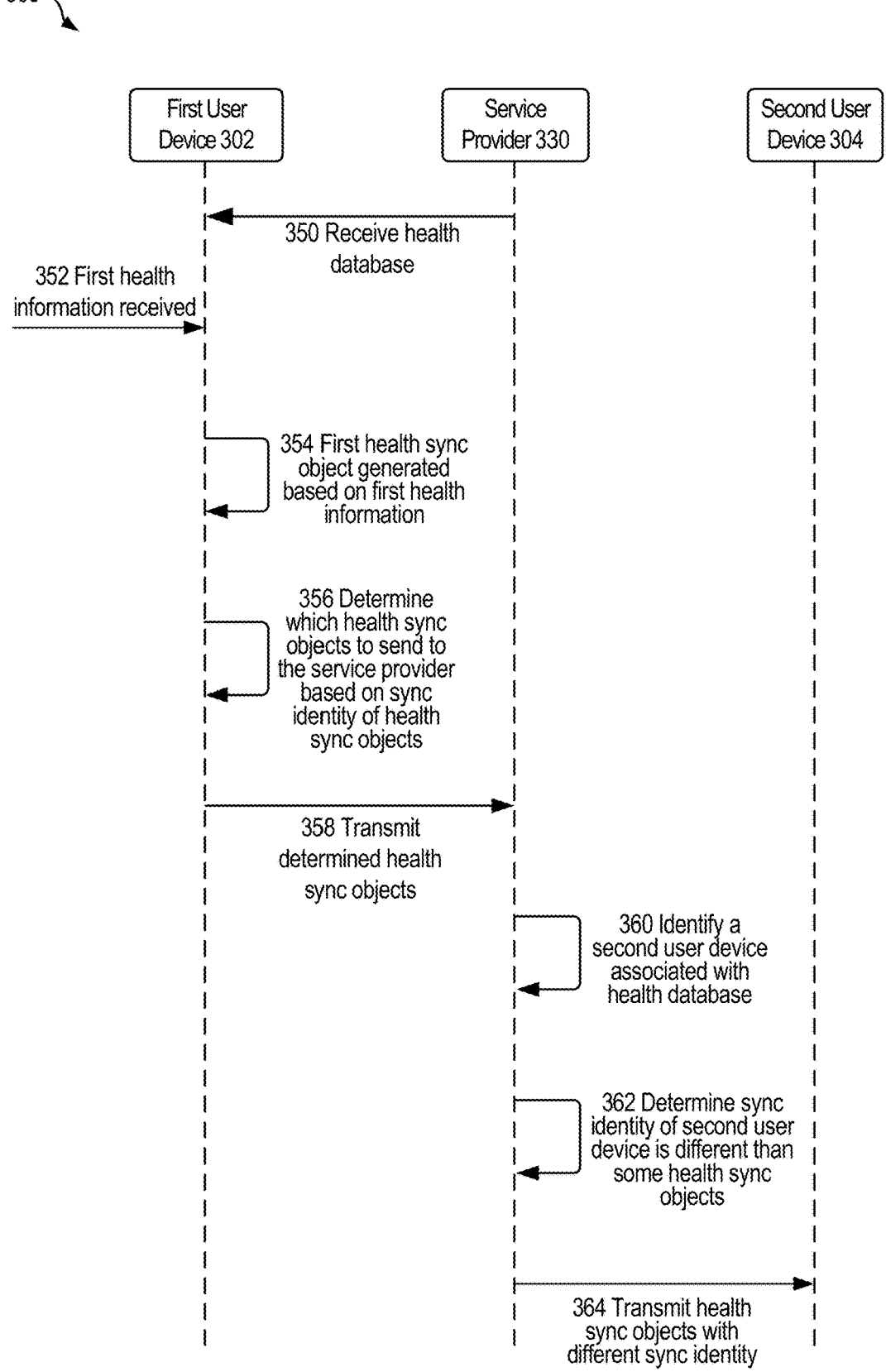
FIG. 3 illustrates a flowchart of a process for synchronizing health information using sync identity across multiple devices, according to at least one example.

FIG. 3 illustrates a flow chart of a process 300 for synchronizing health information using sync identity across multiple devices, according to at least one example. The process 300 includes a) a first user device 302 (for example, the user device 202 of FIG. 2) performing an outgoing synchronization operation transmitting health sync object with a first sync identity to a source of truth (such as service provider 330 which is an example of the service provider 230 of FIG. 2) and b) a source of truth performing an incoming synchronization operation transmitting a first health sync object with a first sync identity to a second user device 304 (for example, the user device 204 of FIG. 2), according to at least one example. When the first user device 302 receives first health information (for example, the first health information 110 of FIG. 1), the first user device 302 can generate a first health sync object with a first sync identity associated with the first user device 302. The first user device 302 can perform an outgoing synchronization operation after determining that the first user device 302 has responsibility to transmit health sync objects with the first sync identity to the service provider 330. The service provider 330 can determine that a second sync identity of the second user device 304 is not the same as the first sync identity of the first health sync object, thus determining to transmit the first health sync object to the second user device 304. The process 300 includes various functions being performed by the various elements shown in FIG. 2. A health application 1110 (FIG. 11), whether embodied in a wearable electronic device 1105 (FIG. 11), a user device 1102 (FIG. 11), or a service provider computer 1104 (FIG. 11), or any suitable combination of the foregoing may perform parts of the process 300 of FIG. 3.

The process 300 can begin at 350, by a first user device 302 (for example, the user device 202 of FIG. 2) associated with a user profile (for example, an account associated with the user 150 of FIG. 1) receiving a health database from a service provider 330 (for example, the service provider 230 of FIG. 2). The health database can be some or all health information at a health information database (for example, the health information database 132 of FIG. 2). The health database can also be referred to as a health information datastore. The health database can be associated with the user profile. In some examples, the service provider 330 can be configured to store the health database. In some examples, the service provider 330 can be configured to communicate with the health information database to receive health information.

At 352, the process 300 can include the first user device 302 receiving first health information associated with the user profile and collected, at least in part, by the first user device 302. In some examples, the first health information can be received by the first user device 302 via a user inputting the first health information into the first user device 302. In some examples, the first health information can be obtained via sensors of the first user device 302. In some examples, the first health information can be collected from a web server. In some examples, the first health information can be obtained from a server accessible through a network such as database from a medical provider. In some examples, the first health information can be obtained from a gateway for a health database system. In some examples, the first health information can be received from another user device which received health information. For example, the other user device can be a secondary device or an accessory device such as a smartwatch. In some examples, the another user device can receive health information via user input or via sensors of the another user device.

At 354, the process 300 can include the first user device 302 generating a first health sync object based on the first health information. The first health sync object can include a first sync identity. The first sync identity can include a first hardware identifier indicative of the first user device 302 and a first database identifier indicative of the health database. In some examples, the first user device 302 can have access to multiple health information databases, for example, a health information database for the owner of the first user device 302 and a health information database for a relative (such as a child, parent, or other family member). In some examples, the first user device 302 can have access to multiple health information databases which may have access to different information about the same user. Each of these health information databases would be associated with different database identifiers.

At 356, the process 300 can include the first user device 302 determining to transmit the health sync objects to the service provider 330 based on the first user device 302 having responsibility to transmit health sync objects with the first sync identity to the service provider 330. The first user device 302 can use the sync identity of health sync objects to determine which health sync objects to sync to the service provider 330 during an outgoing synchronization operation. In some examples, the first user device 302 can sync health objects with the hardware identifier of the first user device 302. For example, the first user device 302 determines to transmit the first health sync object. At 358, the process 300 can include the first user device 302 transmitting the determined health sync object to the service provider 330. For example, the first user device 302 can transmit the first health sync object.

At 360, the process 300 can include the service provider 330 identifying a second user device 304 (for example, the second user device 204 of FIG. 2) to receive the first health sync object. The second user device 304 can be associated with the health database. At 362, the process 300 can include the service provider 330 determining that the first sync identity is different from a second sync identity associated with the second user device 304. Here, the service provider 330 can use the sync identity of health sync objects to determine which health sync objects to sync to user devices during an outgoing synchronization operation.

At 364, the process 300 can include the service provider 330 transmitting the first health sync object to the second user device 304 based on determining that the first sync identity is different from the second sync identity. In some examples, transmitting the first health sync object to the second user device 304 can be further based on the service provider 330 determining that the second user device 304 does not have responsibility to transmit health sync objects with the first sync identity to the service provider 330.

In some examples, the process 300 can further include the first user device 302 receiving a second health sync object. The second health sync object can include a second sync identity that includes a second hardware identifier indicative of a second user device 304 (for example, the second user device 104 of FIG. 1) and a first database identifier indicative of the health database. In some examples, the process 300 can further include the first user device 302 determining to not transmit the second health sync object to the service provider 330 based on the first user device 302 not having responsibility to transmit health sync objects with the second sync identity to the service provider 330. In some examples, the second health sync object is received from the service provider 330, wherein the service provider 330 is configured to transmit the second health sync object to the first user device 302 based on determining that the second sync identity associated with the second health sync object is different from the first sync identity associated with the first user device 302.

In some examples, the process 300 can include the first user device 302 determining to transmit the second health sync object to the service provider 330 based on the first user device 302 having responsibility to transmit health sync objects with the second sync identity to the service provider 330. In some examples, and in relation to FIG. 6 below, the second sync identity can be associated with a secondary user device (for example, the secondary user device 146 of FIG. 1) associated with the first user device 302 which is a primary user device (for example, the primary user device 102 of FIG. 1). The process 300 can further include the first user device 302 transmitting the second health sync object to the service provider 330. The process 300 can include the first user device 302 receiving an indication that the secondary device has not transmitted the first health sync object to the health database in accordance with a timing criteria. The timing criteria can be within a time period of generating the first health sync object, within receiving the first health information used to generate the first health sync object, or within a time period of transmitting the first health sync object to the primary device.

In some examples, the second sync identity can be associated with a second user device 304 (for example, the user device 104 of FIG. 2) and the second user device 304 is inactive. For example, the second user device 304 may have been deactivated, damaged, or unassociated with the profile of the user. Here, the first user device 302 can have responsibility to transmit health sync objects with the second sync identity to the service provider 330. Similarly, the data of the second user device 304, including the health information on the second user device 304, may have been migrated to the first user device 302.

In some examples, the process 300 can further include the service provider 330 receiving a third health sync object. The third health sync object can be associated with a third sync identity. The third sync identity can be associated with a third user device that is no longer active.

In some examples, the process 300 can further include the service provider 330 receiving a second health sync object from the second user device 304. The second health sync object can include a second sync identity. The second sync identity can include a second hardware identifier indicative of the second user device 304 and a first database identifier indicative of the health database. The process 300 can further include the service provider 330 identifying the first user device 302 to receive the second health sync object. The process 300 can further include determining that the second sync identity is different from the first sync identity. The process 300 can further include the service provider 330 transmitting the second health sync object to the first user device 302 based on determining that the second sync identity is different from the first sync identity.

In some examples, the process 300 can further include the service provider 330 identifying a third user device associated with the health database. The third user device can be a secondary device. The process 300 can further include the service provider 330 determining to not transmit the first health sync object to the third user device based on the third user device being a secondary device.

In some examples, the first user device 302 can be a primary device as described herein (for example, in relation to FIG. 6 below). In some examples, the process 300 can further include the service provider 330 identifying a third user device associated with the health database. The third user device can be a secondary device associated with the first user device 302. The process 300 can further include the service provider 330 determining to not transmit the first health sync object to the third user device based on the third user device being a secondary device associated with the first user device 302.

In some examples, the first user device 302 can be a secondary device as described herein (for example, in relation to FIG. 6 below). In some examples, the process 300 can further include the service provider 330 identifying a third user device associated with the health database. The third user device can be a primary device associated with the first user device 302. The process 300 can further include the service provider 330 determining to not transmit the first health sync object to the third user device based on the third user device being a primary device associated with the first user device 302.

FIG. 4 illustrates a flowchart of a process 400 for synchronizing health information using sync identity across multiple devices, according to at least one example. The process 400 includes a user device (for example, the user device 202 of FIG. 2) performing an outgoing synchronization operation transmitting a first health sync object with a first sync identity to a source of truth (for example, the service provider 230 of FIG. 2), according to at least one example. When the user device receives first health information (for example, the first health information 110 of FIG. 1), the user device can generate a first health sync object with a first sync identity associated with the user device. The user device can perform an outgoing synchronization operation after determining that the user device has responsibility to transmit health sync objects with the first sync identity to the service provider. The process 400 is a variation of the process 300, which includes various functions being performed by the various elements shown in FIG. 2. A health application 1110 (FIG. 11), whether embodied in a wearable electronic device 1105 (FIG. 11), a user device 1102 (FIG. 11), or a service provider computer 1104 (FIG. 11), or any suitable combination of the foregoing may perform the process 400 of FIG. 4. Thus, while the process 400 is described as being performed by the user device, it should be understood that both primary user devices (for example, primary user device 202 of FIG. 2) and secondary user devices (for example, secondary user devices 146, 148 of FIG. 2) may perform the process 400 with limited adjustments.

The process 400 can begin at block 402 by a first user device (for example, the user device 202 of FIG. 2) associated with a user profile (for example, an account associated with the user 150 of FIG. 1) receiving a health database from a service provider (for example, the service provider 230 of FIG. 2). The health database can be some or all health information at a health information database (for example, the health information database 132 of FIG. 2). The health database can also be referred to as a health information datastore. The health database can be associated with the user profile. In some examples, the service provider can be configured to store the health database. In some examples, the service provider can be configured to communicate with the health information database to receive health information.

At block 404, the process 400 can include the first user device receiving first health information associated with the user profile and collected, at least in part, by the first user device. In some examples, the first health information can be received by the first user device via a user inputting the first health information into the first user device. In some examples, the first health information can be obtained via sensors of the first user device. In some examples, the first health information can be collected from a web server. In some examples, the first health information can be obtained from a server accessible through a network such as database from a medical provider. In some examples, the first health information can be obtained from a gateway for a health database system. In some examples, the first health information can be received from another user device which received health information. For example, the other user device can be a secondary device or an accessory device such as a smartwatch. In some examples, the another user device can receive health information via user input or via sensors of the another user device.

At block 406, the process 400 can include the first user device generating a first health sync object based on the first health information. The first health sync object can include a first sync identity. The first sync identity can include a first hardware identifier indicative of the first user device and a first database identifier indicative of the health database. In some examples, the first user device can have access to multiple health information databases, for example, a health information database for the owner of the first user device and a health information database for a relative (such as a child, parent, or other family member). In some examples, the first user device can have access to multiple health information databases which may have access to different information about the same user. Each of these health information databases would be associated with different database identifiers.

At block 408, the process 400 can include the first user device determining to transmit the first health sync object to the service provider based on the first user device having responsibility to transmit health sync objects with the first sync identity to the service provider. The first user device can use the sync identity of health sync objects to determine which health sync objects to sync to the service provider during an outgoing synchronization operation. In some examples, the first user device can sync health objects with the hardware identifier of the first user device. At block 410, the process 400 can include the first user device transmitting the first health sync object to the service provider.

In some examples, the process 400 can further include the first user device receiving a second health sync object. The second health sync object can include a second sync identity that includes a second hardware identifier indicative of a second user device (for example, the second user device 104 of FIG. 1) and a first database identifier indicative of the health database. In some examples, the process 400 can further include the first user device determining to not transmit the second health sync object to the service provider based on the first user device not having responsibility to transmit health sync objects with the second sync identity to the service provider. In some examples, the second health sync object is received from the service provider, wherein the service provider is configured to transmit the second health sync object to the first user device based on determining that the second sync identity associated with the second health sync object is different from the first sync identity associated with the first user device.

In some examples, the process 400 can include the first user device determining to transmit the second health sync object to the service provider based on the first user device having responsibility to transmit health sync objects with the second sync identity to the service provider. In some examples and with reference to FIG. 6 below, the second sync identity can be associated with a secondary user device (for example, the secondary user device 146 of FIG. 1) associated with the first user device which is a primary user device (for example, the primary user device 102 of FIG. 1). The process 400 can further include the first user device transmitting the second health sync object to the service provider. The process 400 can include the first user device receiving an indication that the secondary device has not transmitted the first health sync object to the health database in accordance with a timing criteria. The timing criteria can be within a time period of generating the first health sync object, within receiving the first health information used to generate the first health sync object, or within a time period of transmitting the first health sync object to the primary device.

In some examples, the second sync identity can be associated with a second user device (for example, the user device 104 of FIG. 2) and the second user device is inactive. For example, the second user device may have been deactivated, damaged, or unassociated with the profile of the user. Here, the first user device can have responsibility to transmit health sync objects with the second sync identity to the service provider. Similarly, the data of the second user device, including the health information on the second user device, may have been migrated to the first user device.

FIG. 5 illustrates a flowchart of a process 500 for synchronizing health information using sync identity across multiple devices, according to at least one example. The process 500 includes a source of truth (for example, the service provider 239 of FIG. 2) receiving a first health sync object with a first sync identity from a first user device (for example, the first user device 202 of FIG. 2) and performing an incoming synchronization operation transmitting a first health sync object with a first sync identity to a second user device (for example, the second user device 204 of FIG. 2), according to at least one example. When the first user device can generate the first health sync object based on first health information (for example, the first health information 110 of FIG. 1) the first user device received. The service provider can determine that a second sync identity of the second user device is not the same as the first sync identity of the first health sync object, thus determining to transmit the first health sync object to the second user device. The process 500 is a variation of the process 300, which includes various functions being performed by the various elements shown in FIG. 2.

The process 500 can begin at block 502 by the service provider (for example, the service provider 230 of FIG. 2) transmitting a health database to a first user device for example, the user device 202 of FIG. 2). The health database can be some or all health information at a health information database (for example, the health information database 132 of FIG. 2). The health database can also be referred to as a health information datastore. The health database can be associated with the user profile. In some examples, the service provider can be configured to store the health database. In some examples, the service provider can be configured to communicate with the health information database to receive health information.

At block 504, the process 500 can include the service provider receiving a first health sync object from the first user device. The first health sync object can based on first health information collected, at least in part, at the first user device. In some examples, the first health information can be received by the first user device via a user inputting the first health information into the first user device. In some examples, the first health information can be obtained via sensors of the first user device. In some examples, the first health information can be collected from a web server. In some examples, the first health information can be obtained from a server accessible through a network such as database from a medical provider. In some examples, the first health information can be obtained from a gateway for a health database system. In some examples, the first health information can be received from another user device which received health information. For example, the other user device can be a secondary device or an accessory device such as a smartwatch. In some examples, the another user device can receive health information via user input or via sensors of the another user device. The first health sync object can include a first sync identity that includes a first hardware identifier indicative of the first user device and a first database identifier indicative of the health database.

At block 506, the process 500 can include the service provider identifying a second user device (for example, the second user device 204 of FIG. 2) to receive the first health sync object. The second user device can be associated with the health database. At block 508, the process 500 can include the service provider determining that the first sync identity is different from a second sync identity associated with the second user device. Here, the service provider can use the sync identity of health sync objects to determine which health sync objects to sync to user devices during an outgoing synchronization operation.

At block 510, the process 500 can include the service provider transmitting the first health sync object to the second user device based on determining that the first sync identity is different from the second sync identity. In some examples, transmitting the first health sync object to the second user device can be further based on the service provider determining that the second user device does not have responsibility to transmit health sync objects with the first sync identity to the service provider.

In some examples, the process 500 can further include the service provider receiving a third health sync object. The third health sync object can be associated with a third sync identity. The third sync identity can be associated with a third user device that is no longer active.

In some examples, the process 500 can further include the service provider receiving a second health sync object from the second user device. The second health sync object can include a second sync identity. The second sync identity can include a second hardware identifier indicative of the second user device and a first database identifier indicative of the health database. The process 500 can further include the service provider identifying the first user device to receive the second health sync object. The process 500 can further include determining that the second sync identity is different from the first sync identity. The process 500 can further include the service provider transmitting the second health sync object to the first user device based on determining that the second sync identity is different from the first sync identity.

In some examples, the process 500 can further include the service provider identifying a third user device associated with the health database. The third user device can be a secondary device. The process 500 can further include the service provider determining to not transmit the first health sync object to the third user device based on the third user device being a secondary device.

In some examples, the first user device can be a primary device as described herein (for example, in relation to FIG. 6 below). In some examples, the process 500 can further include the service provider identifying a third user device associated with the health database. The third user device can be a secondary device associated with the first user device. The process 500 can further include the service provider determining to not transmit the first health sync object to the third user device based on the third user device being a secondary device associated with the first user device.

In some examples, the first user device can be a secondary device as described herein (for example, in relation to FIG. 6 below). In some examples, the process 500 can further include the service provider identifying a third user device associated with the health database. The third user device can be a primary device associated with the first user device. The process 500 can further include the service provider determining to not transmit the first health sync object to the third user device based on the third user device being a primary device associated with the first user device.

Figure 6:
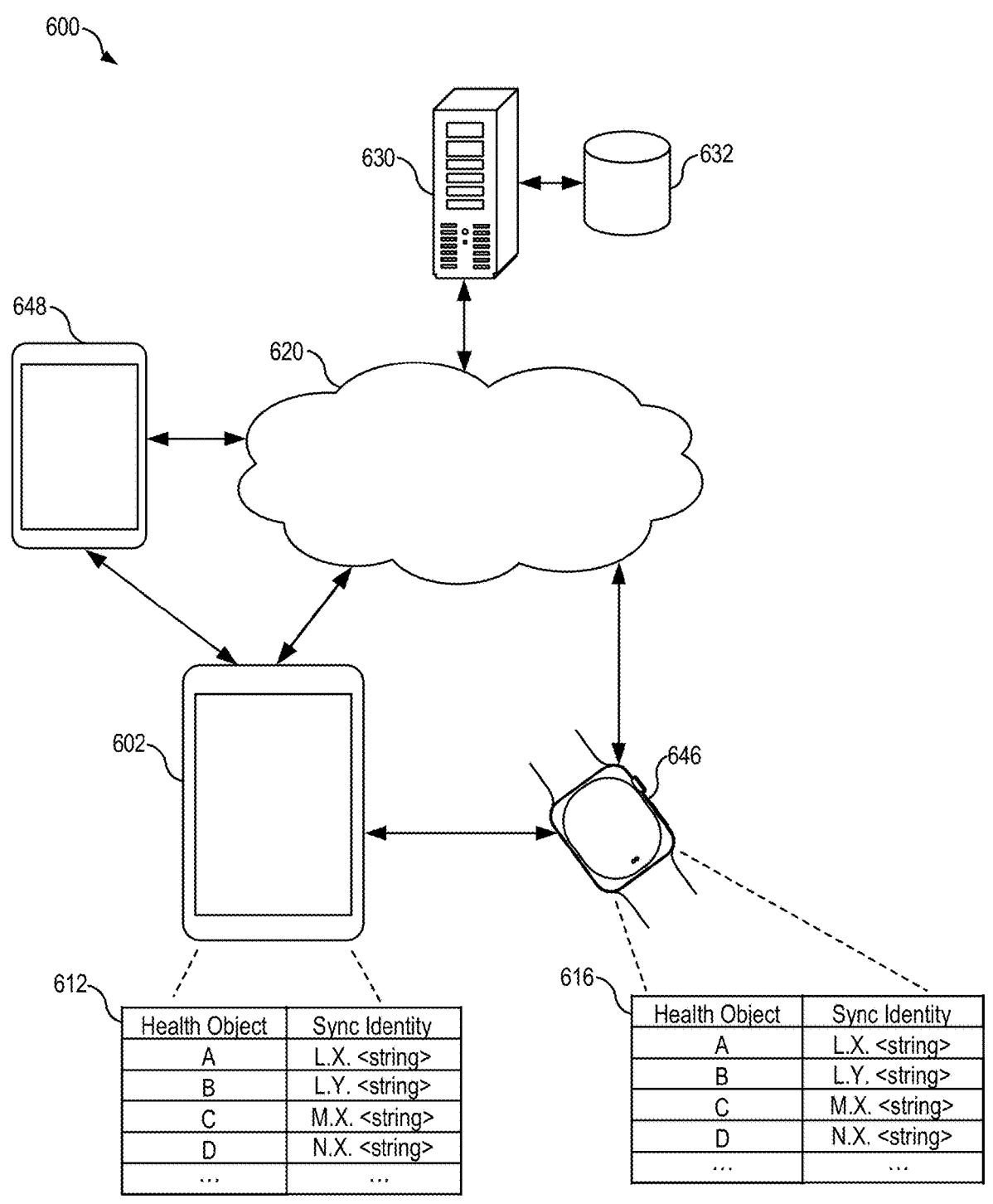
FIG. 6 illustrates a block diagram for synchronizing health information across primary and secondary devices, according to at least one example.

FIG. 6 illustrates a block diagram 600 for synchronizing health information across primary and secondary devices, according to at least one example. The block diagram 600 includes multidevice health information system using the multidevice health information synchronization techniques described herein. The multidevice health information system can include a primary device 602 (for example, primary user device 102 of FIG. 1) that stores health information (for example, health information 110 of FIG. 1) associated with an account of a user (for example, the user 150 of FIG. 1). Health information can include steps taken, calories burned, caloric/food intake, menstrual cycle tracking, medication tracking, health-related recommendations/suggestions, insights regarding the user's health, indications of trends in health data, or any other kind of health information. The health information on the primary device 602 can be synced to an account (for example, a health information account) associated with the user through a service provider 630 (for example, the service provider 130 of FIG. 1).

The primary device 602 can be associated with secondary devices 646, 648 (for example, the secondary user devices 146, 148 of FIG. 1). The secondary devices 646, 648 can also receive health information in the same ways as the primary user device 602 can receive health information as described herein. As described herein, secondary user devices 646, 648 can be devices with limited functionality that is paired with the primary user device 602. In one example, the primary device 602 is a smartphone and the secondary device 646 is a smartwatch. The secondary user device 646 may have limited functionality compared to the primary user device 602 because of hardware or software limitations. For example, the secondary user device 646 may have limited memory, storage, bandwidth, network capability, battery, and/or processing power as compared to the primary user device 602. In another example, a primary device 602 is a smartphone and a secondary device 648 is a smartphone with comparatively limited functionality. Here, the secondary user device 648 may have limited functionality in the form of limited network capabilities, limited processing power, limited battery, or software limitations, or other limitations. The primary user device 602 can be referred to as a parent device and the secondary user devices 646, 648 can be referred to as a child device.

Primary devices 602 and secondary devices 646, 648 can communicate with the service provider 630 through a network 620 (for example, the network 120 of FIG. 1). The network 620 can be any kind of network. For example, the network 620 can be a local area network (LAN) or a wide area network (WAN). The network 620 can be a WiFi network or an equivalent network. The network can be a Bluetooth network or other short-range network connecting only two devices. The network can be a proprietary communication channel between two devices, for example, a communication channel between a phone and a smartwatch.

The account can be accessed through communication with the service provider 630. The health information associated with the account can be stored in a health information database 632 (for example, the health information database 132 of FIG. 1). The service provider 630 can communicate with the health information database 632 and sync health information between the primary devices 602, the secondary devices 646, 648 and the health information database 632. The user can also have other user devices (in addition to the secondary devices 646, 648) that share the same account. As such, the other user devices (including secondary device 646, 648) may also have access to the health information of the user. Each user device can have its own health information datastore associated with the user. User device 602 is illustrated as handheld portable user devices such as smartphones. In some examples, the primary device 602 and secondary devices 646, 648 can be associated with a single user. In some examples, the primary device 602 and secondary devices 646, 648 can be associated with different users, but can all have access to the health information database 632 containing health information associated with the user.

The primary device 602 can have a health information datastore 612. The health information data store can include health sync objects. When the primary device 602 receives new health information, the primary device 602 can generate a health sync object based on the new health information. In some examples, the health information can be received by the primary device 602 via a user inputting the health information into the primary device 602. In some examples, the health information can be obtained via sensors of the primary device 602. In some examples, the health information can be collected from a web server. In some examples, the health information can be obtained from a server accessible through a network such as database from a medical provider. In some examples, the health information can be obtained from a gateway for a health database system. Likewise, the secondary device 646 can have a health information datastore 612. When the secondary device 646 receives new health information, the secondary device 646 can generate a health sync object based on the new health information. In some examples, the health information can be received by the secondary device 646 via a user inputting the health information into the secondary device 646. In some examples, the health information can be obtained via sensors of the secondary device 646. In some examples, the health information can be collected from a web server. In some examples, the health information can be obtained from a server accessible through a network such as database from a medical provider. In some examples, the health information can be obtained from a gateway for a health database system.

The health sync object can include the new health information and/or can include analysis information based on the new health information. In some examples, the new health information can be raw health information including symptoms, heart rate, temperature, blood oxygen, etc. Analysis information can include observations, suggestions, diagnoses, algorithms, predictions based on raw health information, and any other suitable information that can be used as analysis. For example, diagnosing a person to have a disease or condition based on symptoms is an example of analysis information.

When generating the health sync object, the primary device 602 and/or the secondary device 646 includes a sync identity with the health sync object. The sync identity can include a hardware identifier, a database identifier, and an optional instance discriminator. The hardware identifier can be tied to the specific piece of hardware that generated the health sync object. For example, for a health sync object generated on primary device 602, the hardware identifier would be indicative of the primary device 602. The database identifier can be tied to the specific database that to which the health sync object relates. For example, the health sync object can be associated with a first user and the associated health information database associated with that first user. In some examples, a primary device 602 and/or a secondary device 646 can have access to multiple health information databases, for example, a health information database for the owner of the primary device 602 and a health information database for a relative (such as a child, parent, or other family member). In some examples, a primary device 602 and/or a secondary device 646 can have access to multiple health information databases which may have access to different information about the same user. Each of these health information databases would be associated with different database identifiers. The optional instance discriminator can be a string that can be used to differentiate sync identities that might have the same hardware identifier and the same database identifier.

In an example related to FIG. 6, the primary device 602 has a health information datastore 612 including health sync objects (also referred to as health objects) with associated sync identities depicted as a table. In one example, health object A has a sync identity of L.X.<string>. L is indicative of a hardware identifier associated with the primary device 602, which indicates that health object A was generated on primary device 602. X is indicative of a database identifier associated with the owner of the primary device 602, which indicates that the health object A includes health information for a health information database associated with the owner of the user device. <string> is indicative of the instance discriminator. In another example, health object B has a sync identity of L.Y.<string>. Health object B has the same hardware identifier L as health object A, which indicates that the primary device 602 generated both health object A and health object B. However, health object B has a different database identifier Y than health object A. This indicates that health object B is associated with a different database than health object A. In one example, health object B can be associated with a database for a relative (such as a child, parent, or other family member) of the owner of primary device 602. In another example, health object B can be associated with a second health information database associated with the owner of primary device 602. A user can be associated with multiple health information databases for a variety of reasons. In some examples, a user device can have multiple health information datastore that correspond to different database identifiers.

In another example, health object C has a sync identity of M.X.<string>. Health object C has a hardware identifier M which is different from the hardware identifier L of health object A. This indicates that the health object C was generated by a different device than primary device 602, for example, secondary device 646 can be the device that generated health object C. Health object C can have the same database identifier as health object A, indicating that health object C relates to the same database as health object A.

The primary device 602 and the secondary device 646 can use the sync identity of health sync objects to determine which health sync objects to sync to the service provider 630 during an outgoing synchronization operation. As described in relation to user device 202 of FIG. 2, the primary device 602 can sync health sync objects with the associated sync identity of the primary device 602 to the service provider 630. In some examples, the primary device 602 can sync health objects with the hardware identifier of the primary device 602. For example, with reference to the example of health objects A and B above, the primary device 602 can sync health sync objects with sync identity L.X and L.Y to the service provider 630 because the primary device 602 is associated with the hardware identifier L. Likewise, the secondary device 646 can sync health sync objects with the associated sync identity of the secondary device 646. In some examples, the secondary device 646 can sync health objects with the hardware identifier of the secondary device 646. For example, with reference to the example of health object C above, the secondary device 646 can sync health sync objects with sync identity M.X to the service provider 630 because the secondary device 646 is associated with the hardware identifier M.

In some examples, the primary device 602 and the secondary device 646 can be authorized to only sync health sync objects associated with specific health information databases. For example, with reference to the example of health objects A and B above, the primary device 602 can sync health sync object with sync identity L.X to the service provider 630 because the user device 602 is associated with the database identifier X and authorized to sync objects with a database identifier X. On the other hand, the primary device 602 can be associated with database identifier Y and not be authorized to sync objects with database identifier Y.

As such, the primary device 602 does not sync health object B to the service provider 630.

The secondary devices 646, 648 can also use the sync identity of health sync objects to determine which health sync objects to transmit to an associated primary device, such as primary device 602. For example, the secondary device 646 can transmit health sync objects with sync identities associated with the secondary device 646 to primary device 602. For example, with reference to the example of health object C above, the secondary device 646 can transmit health sync objects with sync identity M.X to the primary device 602 because the secondary device 646 is associated with the hardware identifier M. In some examples, the secondary device 646 can connect, transmit, and receive information (including health sync objects) from the primary device 602 via a communication channel that is less resource intensive. For example, the primary device 602 and the secondary device 646 can communicate over a local area network (e.g., WiFi) or a short range communication medium (e.g., Bluetooth). This compares to a long range communication medium that may be more resource intensive such as a cellular network.

Additionally, the user device 602 can also have responsibility to sync health sync objects with other sync identities to the service provider. The user device 602 can have responsibility to sync health sync objects with hardware identifiers for associated secondary devices such as secondary devices 646, 648. In some examples, the secondary devices 646, 648 can transmit health sync objects with their associated sync identities to the service provider 630 in accordance with a timing criteria. For example, the secondary devices 646, 648 may be able to transmit a health sync object with the associated sync identities of the secondary devices 646, 648 to the service provider 630 in accordance with a timing criteria constituting within three days of generating the health sync object. The timing criteria can be within 5 minutes, 10 minutes, 15 minutes, 20 minutes, 30 minutes, 1 hour, 2 hours, 3 hours, 4 hours, 5 hours, 6 hours, 12 hours, 24 hours, 2 days, 3 days, 4 days, 5 days, 7 days, 8 days, 10 days, 14 days, 3 weeks, 4 weeks, or one month, or any amount of time in between, of generating the health sync object. The timing criteria can be within 5 minutes, 10 minutes, 15 minutes, 20 minutes, 30 minutes, 1 hour, 2 hours, 3 hours, 4 hours, 5 hours, 6 hours, 12 hours, 24 hours, 2 days, 3 days, 4 days, 5 days, 7 days, 8 days, 10 days, 14 days, 3 weeks, 4 weeks, or one month, or any amount of time in between, of receiving the health information used to generate the health sync object. The timing criteria can be within 5 minutes, 10 minutes, 15 minutes, 20 minutes, 30 minutes, 1 hour, 2 hours, 3 hours, 4 hours, 5 hours, 6 hours, 12 hours, 24 hours, 2 days, 3 days, 4 days, 5 days, 7 days, 8 days, 10 days, 14 days, 3 weeks, 4 weeks, or one month, or any amount of time in between, of receiving the health information used to generate the health sync object. The timing criteria can be within 5 minutes, 10 minutes, 15 minutes, 20 minutes, 30 minutes, 1 hour, 2 hours, 3 hours, 4 hours, 5 hours, 6 hours, 12 hours, 24 hours, 2 days, 3 days, 4 days, 5 days, 7 days, 8 days, 10 days, 14 days, 3 weeks, 4 weeks, or one month, or any amount of time in between, of transmitting the health sync object to the primary device 602.

In some examples, the secondary devices 646, 648 are unable to transmit health sync objects with the associated sync identities of the secondary devices 646, 648 to the service provider 630 in accordance with the predetermined timing criteria because the secondary devices 646, 648 have limited memory, storage, bandwidth, network capability, battery, and/or processing power. In such examples, a primary device can transmit health sync objects with a sync identity of an associated secondary device to the service provider. For example, the primary device 602 can transmit health sync objects with a sync identity M.X associated with the secondary device 646 to the service provider 630 on behalf of the secondary device 646.

In some examples, the primary device 602 can determine, in accordance with a timing criteria, that the secondary device 646 has not transmitted a particular health sync object to the service provider. In some examples, the primary device 602 transmitting a request to the secondary device for an indication whether the secondary device has transmitted a particular health sync object to the service provider. If the primary device 602 does not receive a response (for example, an indication that the secondary device 646 has or has not transmitted the particular health sync object to the service provider 630) within a second time period, the primary device can transmit the health sync objects associated with the secondary device 646 to the service provider. This second time period can be 5 minutes, 15 minutes, 30 minutes, 1 hour, 2 hours, 3 hours, 6 hours, 12 hours, 1 day, 2 days, 3 days, 4 days, 5 days, 7 days, 8 days, 10 days, 2 weeks, 1 month, or any amount of time in between. In some examples, the secondary device 646 can determine that the secondary device 646 has not transmitted a particular health sync object to the service provider 630 in accordance with a timing criteria. In some examples, the secondary device transmit, to the primary device 602, an indication that the secondary device has not transmitted the first health sync object to the service provider. The indication can be configured to cause the primary device 602 to transmit the particular health sync object to the service provider 630. In some examples, the indication and/or request can relate to two or more health sync objects generated by the secondary device 646.

The timing criteria can be important because secondary devices may have a limited health information datastore when compared to primary devices. In some examples, a secondary device may have a health information datastore that only includes health information from a last time period. For example, secondary device 646 may have a health information data store that only includes health information for the last eight days. The last time period can be the last year, six months, 3 months, 2 months, 1 month, 8 weeks, 4 weeks, 2 weeks, 10 days, 8 days, 7 days, 5 days, 4 days, 3 days, 2 days, 1 day, or any time period in between. Once health information is associated with a time outside the last time period, the health information can be deleted on the secondary device 646. In this way, the timing criteria to transmit to the service provider can ensure that health information received by the secondary device 646 is not lost once the secondary device 646 deletes the health information.

In this way, outgoing synchronization operations can be limited to health objects with sync identities associated with the user device performing the outgoing synchronization operation. This can limit redundant transmissions of health information within the multidevice health information system and thus limited the use of resources of the service provider 630 and the user devices 602, 604. Such resources can include bandwidth, network, computing/processing power, and/or battery life of the service provider 630 and/or the user device 602, 604. In this way, the user device can trust that another user device has responsibility for health sync object not generated by the user device.

FIG. 7 illustrates a flow chart showing a process 700 for synchronizing health information across primary and secondary devices, according to at least one example. The process 700 includes a primary device 702 (for example, the primary user device 602 of FIG. 6) transmitting to a service provider 730 (for example, the service provider 630 of FIG. 6), a health sync object generated by a secondary device 746 (for example, the secondary user device 646 of FIG. 6), according to at least one example. The secondary device 746 receives health information (for example, health information 112 of FIG. 1) and generates the health sync object. The secondary device 746 can be configured to transmit the health sync object to the service provider 730. However, due to resource constraints such as network capabilities, bandwidth, power, and/or battery life, the secondary device 746 may not be able to transmit the health sync object to the service provider 730. The secondary device 746 can transmit the health sync object to the primary device 702. Once a timing criteria has not been met in relation to the secondary device 746 transmitting the health sync object to the service provider 730, the primary device 702 can transmit the health sync object to the service provider 730. The process 700 includes various functions being performed by the various elements shown in FIG. 6. A health application (for example, the health application 1110 of FIG. 11) on the primary device 702 may perform the process 800 of FIG. 8.

The process 700 can begin at 750, by a secondary device 746 receiving first health information associated with a user profile. The user profile can be associated with a health database that is stored by a service provider 730. In some examples, the secondary device 746 has a store of health information limited to health information associated with the health database from a last time period. In some examples, the secondary device 746 deletes health information associated with a time outside the last time period.

At 752, the process 700 can include the secondary device 746 generating a first health sync object based on the first health information. The first health sync object can include a first sync identity that includes a first hardware identifier indicative of the secondary device 746 and a first database identifier indicative of the health database. The secondary device 746 can be configured to transmit the first health sync object to the service provider 730. The primary device 702 can be configured to generate a second health sync object including a second sync identity that includes a second hardware identifier indicative of the primary device 702 and the first database identifier. The primary device 702 can be configured to transmit the second health sync object to the service provider 730. The primary device 702 can be configured to have responsibility to transmit health sync objects with the first sync identity and health sync objects with the second sync identity to the service provider 730.

At 754, the process 700 can include the secondary device 746 transmitting the first health sync object to a primary device 702. The secondary device 746 can also use the sync identity of health sync objects to determine which health sync objects to transmit to the primary device 702. For example, the secondary device 746 can transmit health sync objects with sync identities associated with the secondary device 746 to primary device 702. In some examples, the secondary device 746 can transmit and receive information from the primary device 702 over a short-range communication medium.

At 756, the process 700 can include the primary device 702 determining, in accordance with a timing criteria, that the secondary device 746 has not transmitted the first health sync object to the service provider 730. The timing criteria can be within a time period of generating the first health sync object, within receiving the first health information used to generate the first health sync object, or within a time period of transmitting the first health sync object to the primary device 702.

At 758, the process 700 can include the primary device 702 transmitting a request to the secondary device 746 for an indication whether the secondary device 746 has transmitted the first health sync object to the service provider 730. In some examples, the primary device 702 does not receive a response (for example, an indication that the secondary device 746 has or has not transmitted the particular health sync object to the service provider 730) within a time period, the primary device 702 can transmit the health sync objects associated with the secondary device 746 to the service provider 730.

At 760, the process 700 can include the secondary device 746 determining, in accordance with a timing criteria, that the secondary device 746 has not transmitted the first health sync object to the service provider 730. The timing criteria can be within a time period of generating the first health sync object, within receiving the first health information used to generate the first health sync object, or within a time period of transmitting the first health sync object to the primary device 702.

In some examples, the process 700 includes only one of steps 756, 758, and 760. In some examples, the process 700 includes only two of steps 756, 758, and 760.

At 762, the process 700 can include the secondary device 746 transmitting, to the primary device 702, an indication that the secondary device 746 has not transmitted the first health sync object to the service provider 730. The indication can be configured to cause the primary device 702 to transmit the first health sync object to the service provider 730. At 764, the process 700 can include the primary device 702 transmitting the first health sync object to the service provider 730.

In some examples, the process 700 can further include the primary device 702 transmitting a request to the secondary device 746 for an indication whether the secondary device 746 has transmitted the first health sync object to the service provider 730.

In some examples, the process 700 can further include the primary device 702 receiving a second health information associated with the user profile. The process 700 can further include the primary device 702 generating a second health sync object based on the second health information. The second health sync object can include a second sync identity that includes a second hardware identifier indicative of the primary device 702 and the first database identifier. The process 800 can further include the primary device 702 transmitting the second health sync object to the service provider 730.

In some examples, the process 700 can further include the secondary device 746 receiving, from the primary device 702, a request for an indication whether the secondary device 746 has transmitted the first health sync object to the service provider 730.

In some examples, the process 700 can further include the secondary device 746 receiving second health information associated with the user profile. The process 700 can further include the secondary device 746 generating a second health sync object based on the second health information. The second health sync object can include the first sync identity. The process 700 can further include the secondary device 746 transmitting the second health sync object to the service provider 730.

In some examples, the secondary device 746 can be configured to have a store of health information limited to health information associated with the health database from a last time period. In some examples, the secondary device 746 can be configured to delete health information associated with a time outside the last time period.

FIG. 8 illustrates a flowchart of a process 800 for synchronizing health information across primary and secondary devices, according to at least one example. The process 800 includes a primary device (for example, the primary user device 602 of FIG. 6) transmitting to a service provider (for example, the service provider 630 of FIG. 6), a health sync object generated by a secondary device (for example, the secondary user device 646 of FIG. 6), according to at least one example. The secondary device receives health information (for example, health information 112 of FIG. 1) and generates the health sync object. The secondary device can be configured to transmit the health sync object to the service provider. However, due to resource constraints such as network capabilities, bandwidth, power, and/or battery life, the secondary device may not be able to transmit the health sync object to the service provider. The secondary device can transmit the health sync object to the primary device. Once a timing criteria has not been met in relation to the secondary device transmitting the health sync object to the service provider, the primary device can transmit the health sync object to the service provider. A health application (for example, the health application 1110 of FIG. 11) on the primary device may perform the process 800 of FIG. 8. The process 800 is a variation of the process 700, which includes various functions being performed by the various elements shown in FIG. 6.

The process 800 can begin at block 802 by the primary device receiving a first health sync object based on first health information associated with a user profile associated with a health database. A service provider can be configured to store the health database. The first health sync object can include a first sync identity which includes a first hardware identifier indicative of the secondary device and a first database identifier indicative of the health database. The secondary device can be configured to transmit the first health sync object to the service provider.

At block 804, the process 800 can include the primary device receiving an indication that the secondary device has not transmitted the first health sync object to the service provider in accordance with a timing criteria. The timing criteria can be within a time period of generating the first health sync object, within receiving the first health information used to generate the first health sync object, or within a time period of transmitting the first health sync object to the primary device. In some examples, the primary device can transmit and receive information from the secondary device over a short-range communication medium.

At block 806, the process 800 can include the primary device transmitting the first health sync object to the service provider. In some examples, the primary device can have responsibility to transmit, to the service provider, health sync objects with the first sync identity and health sync objects with a second sync identity. The second sync identity can be associated with a third user device that is no longer active. In some examples, the primary device can have responsibility to transmit, to the secondary device, health sync objects with sync identities other than the first sync identity.

In some examples, the process 800 can further include the primary device transmitting a request to the secondary device for an indication whether the secondary device has transmitted the first health sync object to the service provider.

In some examples, the secondary device can be configured to have a store of health information limited to health information associated with the health database from a last time period. In some examples, the secondary device can be configured to delete health information associated with a time outside the last time period.

In some examples, the process 800 can further include the primary device receiving a second health information associated with the user profile. The process 800 can further include the primary device generating a second health sync object based on the second health information. The second health sync object can include a second sync identity that includes a second hardware identifier indicative of the primary device and the first database identifier. The process 800 can further include the primary device transmitting the second health sync object to the service provider.

FIG. 9 illustrates a flowchart of a process 900 for synchronizing health information across primary and secondary devices, according to at least one example. The process 900 includes a secondary device (for example, the secondary user device 646 of FIG. 6) transmitting to a primary device (for example, the primary user device 602 of FIG. 6), an indication to transmit a health sync object generated by a secondary device to the service provider, according to at least one example. The secondary device receives health information (for example, health information 112 of FIG. 1) and generates the health sync object. The secondary device can be configured to transmit the health sync object to the service provider. However, due to resource constraints such as network capabilities, bandwidth, power, and/or battery life, the secondary device may not be able to transmit the health sync object to the service provider. The secondary device can transmit the health sync object to the primary device. Once a timing criteria has not been met in relation to the secondary device transmitting the health sync object to the service provider, the secondary device can transmit an indication to the primary device to transmit the health sync object to the service provider. The process 900 is a variation of the process 700, which includes various functions being performed by the various elements shown in FIG. 6. A health application (for example, the health application 1110 of FIG. 11) on the secondary device may perform the process 900 of FIG. 9.

The process 900 can begin at block 902 by a secondary device receiving first health information associated with a user profile. The user profile can be associated with a health database that is stored by a service provider. In some examples, the secondary device has a store of health information limited to health information associated with the health database from a last time period. In some examples, the secondary device deletes health information associated with a time outside the last time period.

At block 904, the process 900 can include the secondary device generating a first health sync object based on the first health information. The first health sync object can include a first sync identity that includes a first hardware identifier indicative of the secondary device and a first database identifier indicative of the health database. The secondary device can be configured to transmit the first health sync object to the service provider. The primary device can be configured to generate a second health sync object including a second sync identity that includes a second hardware identifier indicative of the primary device and the first database identifier. The primary device can be configured to transmit the second health sync object to the service provider. The primary device can be configured to have responsibility to transmit health sync objects with the first sync identity and health sync objects with the second sync identity to the service provider.

At block 906, the process 900 can include the secondary device transmitting the first health sync object to a primary device. The secondary device can also use the sync identity of health sync objects to determine which health sync objects to transmit to the primary device. For example, the secondary device can transmit health sync objects with sync identities associated with the secondary device to primary device. In some examples, the secondary device can transmit and receive information from the primary device over a short-range communication medium.

At block 908, the process 900 can include the secondary device determining, in accordance with a timing criteria, that the secondary device has not transmitted the first health sync object to the service provider. The timing criteria can be within a time period of generating the first health sync object, within receiving the first health information used to generate the first health sync object, or within a time period of transmitting the first health sync object to the primary device.

At block 910, the process 900 can include the secondary device transmitting, to the primary device, an indication that the secondary device has not transmitted the first health sync object to the service provider. The indication can be configured to cause the primary device to transmit the first health sync object to the service provider.

In some examples, the process 900 can further include the secondary device receiving, from the primary device, a request for an indication whether the secondary device has transmitted the first health sync object to the service provider.

In some examples, the process 900 can further include the secondary device receiving second health information associated with the user profile. The process 900 can further include the secondary device generating a second health sync object based on the second health information. The second health sync object can include the first sync identity. The process 900 can further include the secondary device transmitting the second health sync object to the service provider.

Figure 10:
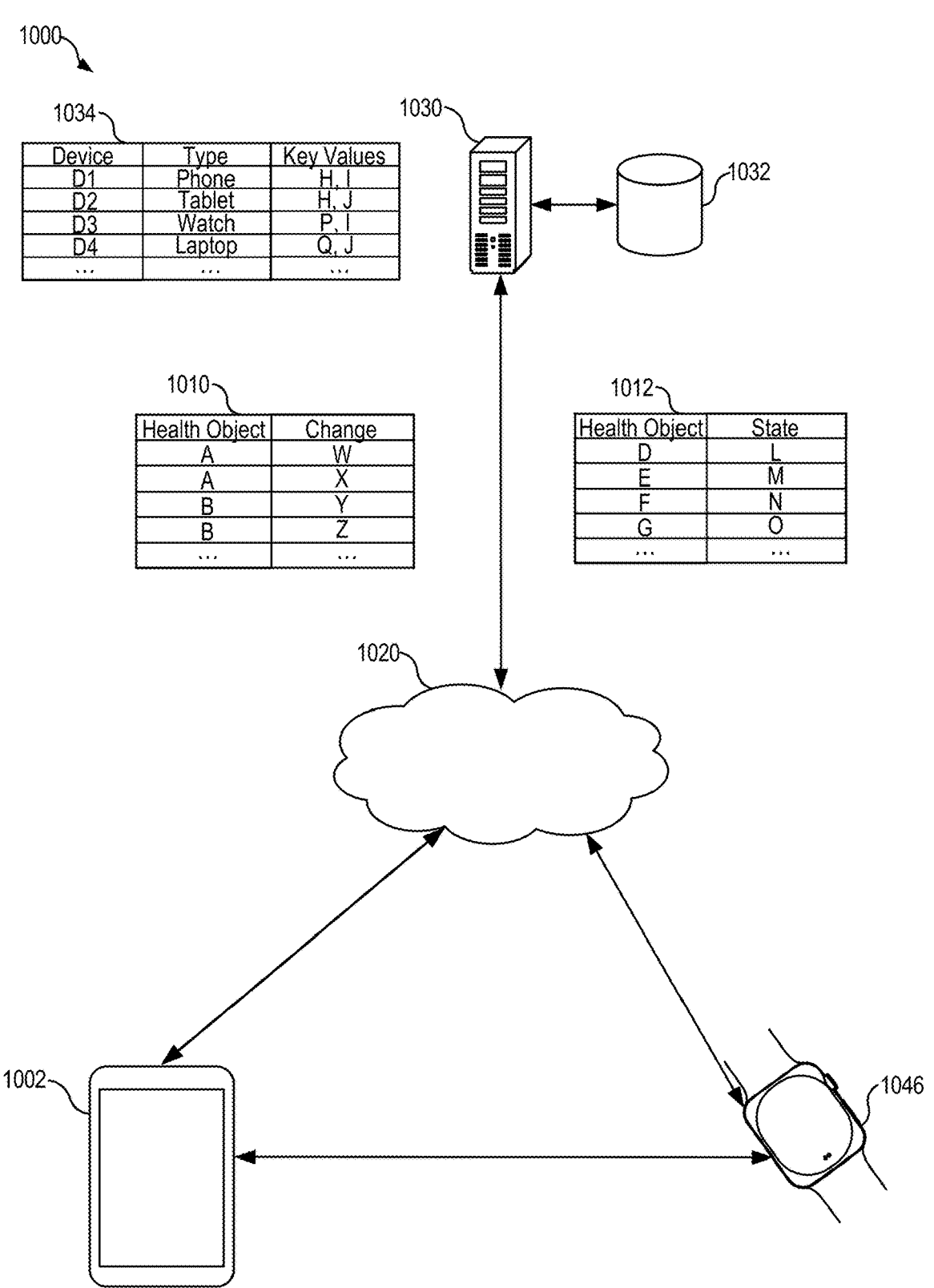
FIG. 10 illustrates a block diagram for synchronizing health information across multiple devices using various synchronization methods, according to at least one example.

FIG. 10 illustrates a block diagram 1000 for synchronizing health information across multiple devices using various synchronization methods, according to at least one example. The block diagram 1000 includes a multidevice health information system using the multidevice health information synchronization techniques described herein. The multidevice health information system can include a user device 1002 (for example, the first user device 102 of FIG. 1) that stores health information (for example, health information 110 of FIG. 1) associated with an account of a user (for example, the user 150 of FIG. 1). Health information can include steps taken, calories burned, caloric/food intake, menstrual cycle tracking, medication tracking, health-related recommendations/suggestions, insights regarding the user's health, indications of trends in health data, or any other kind of health information. The health information on the primary device 1002 can be synced to an account (for example, a health information account) associated with the user through a service provider 630 (for example, the service provider 130 of FIG. 1).

The account can be accessed through communication with the service provider 1030. The health information associated with the account can be stored in a health information database 1032 (for example, the health information database 132 of FIG. 1). The service provider 1030 can communicate with the health information database 1032 and sync health information between the user devices 1002, 1046 and the health information database 1032. The user can also have other user devices, such as user device 1046 (for example, user device 146 of FIG. 1), that share the same account. As such, the other user device 1046 may also have access to the health information of the user. Each user device can have its own health information datastore associated with the user. User device 1002 is illustrated as handheld portable user devices such as smartphones while user device 1046 is illustrated as a smartwatch. As described herein, an example user device can be any suitable user device such as a smartphone, tablet, media player, laptop, wearable device, smartwatch, and the like. In some examples, the user devices 1002, 1046 can be associated with a single user. In some examples, the user devices 1002, 1046 can be associated with different users, but can all have access to the health information database 1032 containing health information associated with the user.

The techniques described herein also enable user devices 1002, 1046 to perform outgoing and incoming synchronization operations to the service provider 1030 through one or more synchronization methods. Different types of health information can be synchronized (either in an outgoing or an incoming operation) by different synchronization methods. Example types of health information can include streaming information, state information, and analysis information. In some examples, streaming information can be synchronized (also referred to as synced) via a changes sync method. In some examples, state information can be synced via a state sync method. In some examples, analysis information can be synced via a context sync method.

Streaming information can include information representing changes over time. For example, streaming information can include step tracking, calorie burning, medications taken over time, heart rate, and any other suitable data or information that changes over time. Streaming data can be considered unbounded because streaming data does not represent an absolute state of the information but rather the changes from a previous state. Health information from a user device that represents streaming information can be synced to the service provider and eventually other user devices via the changes sync method. The changes sync method can transmit the changes in the health information to the service provider via an outgoing synchronization operation.

The changes sync method can also include the service provider transmitting the changes in health information to other user devices via an incoming synchronization operation. For example, health information 1010 can be health information that is synced via the changes sync method. Here, health information 1010 represents streaming information in an outgoing synchronization operation to user device 1002. Health Object A has a change W and a change X that relate to health object A. When performing outgoing synchronization operation to user device 1002 of the health object A, both of the changes W and X to health object A have to be synchronized to user device 1002 in order for user device 1002 to have the complete information regarding health object A. Likewise, health object B has a change Y and a change Z that relate to health object B. When performing outgoing synchronization operation to user device 1046 of the health object B, both of the changes Y and Z to health object B have to be synchronized to user device 1046 in order for user device 1046 to have the complete information regarding health object B.

In this way, the changes sync method represents a stream of changes in health information that are periodically synchronized across the service provider 1030 and the user devices 1002, 1046. To keep this type of streaming information synchronized across multiple devices via the changes sync method can be taxing on bandwidth consumption, network resources, computing/processing power, and battery life of the user devices when used for all types of health information. As such the changes sync method may only be used for important health information or health information that may be best represented as a log of changes. Example health information that may be best represented as a log of changes includes step tracking, calorie burning, heart rate, etc. However, the changes sync method may not be optimal when a device has limited resources for bandwidth, network, computing/processing power, and/or battery life. For example, synchronizing health information via the changes sync method to user device 1046, a smartwatch, may be too demanding on the resources of user device 1046 such as bandwidth, network, and battery life. For this reasons, synchronizing state information via a state sync method as described herein may be more optimal when synchronizing health information to a device such as user device 1046.

Another type of health information can be state information. State information represents a bounded piece of information that represents the actual state of the information. State information is different than streaming information which is meant to convey the changes that have occurred. In some examples, state information is bounded to a time window such that the state information represents the actual state during that time window. For example, a current list of medications a user uses can be stored as state information because the current list of medications represents an actual state of the list of medications. An example of streaming information related to a list of medications could be the changes in the dosage of medication or changes in the medication over time. Other examples of state information can include a list of diseases, ailments, and conditions of a user at a particular time.

State information can be synchronized between the user devices 1002, 1046 and the service provider 1030 via a state sync method. The state sync method can be used to sync state information across the multidevice health information system. The state sync method enables user devices 1002, 1046 and the service provider 1030 to transmit the actual state of health information rather than the changes in health information over time (for example, streaming information described herein). The state sync method may provide a high-level of consistency and accuracy for health information represented as state information across the multiple user devices because each user device can know that the state information represents actual health information rather than a stream of changes to health information as seen with streaming information. The state sync method also can reduce the resources needed at the user devices 1002, 1046 and service provider 1030 to synchronize health information by reducing the need to constantly transmit and receive changes to health information. This can be seen with regards to health object A in health information 1010 which needed to include both changes W and X while health object D in health information 1012 only needed the state L. As more changes are logged in relation to a health object, the more health information will need to be transmitted and received across the multidevice health information system in order to maintain consistent information across the multiple devices.

In some examples, streaming information can be bounded into state information. In one example a user's medication history is a stream of medication names and doses taken which represents streaming information. The stream of doses taken can be bounded into a window of the history of the stream of doses taken during a specific time window. By bounding the stream of doses take in into a window the dose history becomes a state that can be synchronized via the state sync method.

With reference to FIG. 10, health information 1012 can be health information that is synced via the state sync method. Here, health information 1012 represents state information (also referred to as bounded information) in an outgoing synchronization operation to user device 1002. Health Object D has a state L. When performing outgoing synchronization operation to user device 1002 of the health object D, only the state L of health object D has to be synchronized to user device 1002 in order for user device 1002 to have the complete information regarding health object D. Likewise, health object E has a state M. When performing outgoing synchronization operation to user device 1046 of the health object E, only the state M of health object E has to be synchronized to user device 1046 in order for user device 1046 to have the complete information regarding health object E.

Synchronizing health information via the state sync method can be less resource intensive than the change sync method. For example, the change sync method can involve sending a stream of changes to the health information over time in order to make the health information eventually consistent across multiple devices. In one example, tracking medications taken through change sync can include an update for each time a medication was taken. This type of synchronization can be demanding on bandwidth, network, computing/processing power, and/or battery life at the user devices and/or the service provider. Alternatively, tracking medication taken as a state represents a state of the medications taken at a specific time or during a specific window. State synchronization can be consistent across the multidevice health information system relatively quickly because the synchronization of the health information represents a picture of the health information at a specific time rather than a best effort delivery of changes to the health information over time.

Another type of health information can be stored both at the user devices and at the service provider as analysis information. Analysis information includes observations, suggestions, diagnoses, algorithms, predictions based on raw health information, and any other suitable information that can be used as analysis. For example, diagnosing a person to have a disease or condition based on symptoms is an example of analysis information. Analysis information is highly dependent on the algorithms and/or processing of raw health information. Raw health information can include symptoms, heart rate, temperature, blood oxygen, etc. However, algorithms for different health applications can change as the version of the application changes. The algorithm can also be different based on the computing and/or other resources on the user device or can change due to updates in science/understanding. In order to synchronize analysis information across multiple devices with potentially different algorithms, the applicable health information can be synchronized through a context sync method.

In order to generate consistent analysis information across the multidevice health information system, the service provider needs to understand the context of each user device. The service provider can store device information regarding each user device. For example, the service provider can store the type of user device such as whether a user device is a smartphone, smartwatch, laptop, tablet, etc. An example of device information can be seen at device information 1034, which includes a device identifier (or name), a device type, and key values. The service provider 1030 can store the device information 1034 for all devices associated with a user account, the service provider 1030, and the health information database 1032. The device identifier can be some kind of unique identifier for the device. The device type can include types such as smartphones, tablets, smartwatches, laptops, and other types of user devices. By storing device information, a more intelligent synchronization of the health information can be enabled. A more intelligent synchronization of the health information can reduce power consumption needs when synchronizing the health information across multiple devices. Each device can see a reduction in power consumption for synchronization of the health information.

Analysis information can be synchronized between the user devices 1002, 1046 and the service provider 1030 via a context sync method. One way in which the context sync method can be used is to sync analysis information across the multidevice health information system. The context sync method can be used to create consistent analysis information from the multidevice health information system by merging analysis information from multiple user devices which may have generated different analysis information based on each user devices' algorithms. Software and/or applications on the user devices and service provider can use the device context record and the device-specific key value data when determining how to merge health information (for example, analysis information) across a user's health information database. User devices are able to query the key value data of other devices and the device context records of other devices for synchronization operations. In some examples, the service provider 1030 will use the device information and/or associated key values to determine that a particular device of the user devices has access to a more accurate and/or more precise algorithm such that the service provider will merge the analysis information by choosing to store the analysis information from the particular device. The service provider 1030 can then perform incoming synchronization operations to send that analysis information back out to all user devices in the multidevice health information system.

The service provider 1030 can receive the device information when the user device is setup to connect to the multidevice health information system. For example, when user device 1002 first enables synchronization of health data to the service provider 1030 through an account, the user device 1002 (or software on the user device) can create a device context record and send the device context record to the service provider. The device context record can include device information such as a device unique identifier and/or a device type. The device context records can be stored in a database table (such as the device information 1034) at the service provider 1030.

Other device specific information can also be useful for the service provider 1030 and/or user devices 1002, 1046 of the multidevice health information system. For example, the service provider 1030 can also store device-specific key value data that can be useful for software and applications on user devices. Example key value data can include other device specific information such as an operating system version for the operating system on the device and/or an application version for the application on the device. User devices 1002, 1046 and/or the service provider 1030 can query the service provider 1030 for the device-specific key value data of user devices in the multidevice health information system. The key values can be designated by software and/or applications on the user devices 1002, 1046.

The context sync method can also be used in tandem with other synchronization methods in order to determine the best times and/or circumstances to synchronize health information to and from particular user devices 1002, 1046. For example, the service provider 1030 can use device information to determine that a particular user device 1046 is a smartwatch with limited resources. The service provider 1030 can determine when not to synchronize health information to a particular user device and/or when to synchronize health information to a particular user device. For example, the service provider 1030 may perform incoming synchronization operations less often if the receiving user device is a smartwatch or other device with limited functionality such as a secondary device. Alternatively, the service provider 1030 may determine to perform incoming synchronization operations to the primary device rather than to the secondary device. In such circumstances, the primary device can then synchronize the health information to the secondary device.

Figure 11:
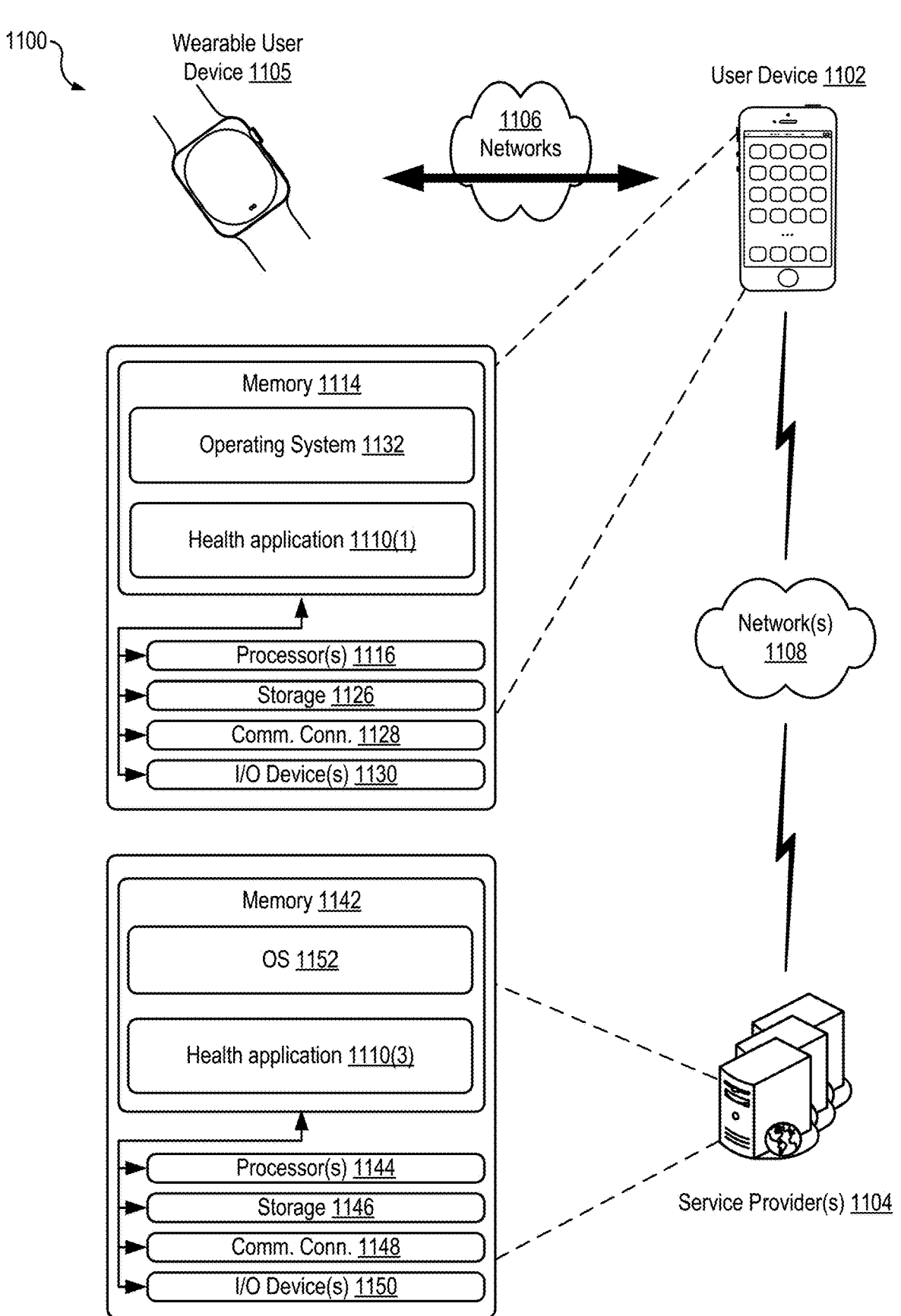
FIG. 11 illustrates an example architecture or environment configured to implement techniques relating to conducting sharing of health data updates among user devices and identifying changes in health data, according to at least one example.

FIG. 11 illustrates an example architecture or environment 1100 configured to implement techniques relating to conducting sharing of health data updates among user devices, according to at least one example. In some examples, the example architecture 1100 may further be configured to enable a user device 1102 (e.g., the user device 102, 104, 106, 146, 148), the service provider computers 1104 (e.g., the service provider 130), and a wearable electronic device 1105 (e.g., an example secondary device such as secondary device 146) to share information. In some examples, the devices may be connected via one or more networks 1108 and/or 1106 (e.g., via Bluetooth, WiFi, the Internet, or the like). In the architecture 1100, one or more users may utilize the user device 1102 to manage, control, or otherwise utilize the wearable electronic device 1105, via the one or more networks 1106. Additionally, in some examples, the wearable electronic device 1105, the service provider computers 1104, and the user device 1102 may be configured or otherwise built as a single device. For example, the wearable electronic device 1105 and/or the user device 1102 may be configured to implement the examples described herein as a single computing unit, exercising the examples described above and below without the need for the other devices described.

In some examples, the networks 1106, 1108 may include any one or a combination of many different types of networks, such as cable networks, the Internet, wireless networks, cellular networks, satellite networks, other private and/or public networks, or any combination thereof. While the illustrated example represents the user device 1102 accessing the service provider computers 1104 via the networks 1108, the described techniques may equally apply in instances where the user device 1102 interacts with the service provider computers 1104 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 1102 may be configured to collect and/or manage user activity data potentially received from the wearable electronic device 1105. In some examples, the wearable electronic device 1105 may be configured to provide health, fitness, activity, and/or medical data of the user to a third- or first-party application (e.g., the service provider computer 1104). In turn, this data may be used by the user device 1102 to identify trends and/or for sharing. The user device 1102 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 1102 may be in communication with the service provider computers 1104 and/or the wearable electronic device 1105 via the networks 1108, 1106, or via other network connections.

In one illustrative configuration, the user device 1102 may include at least one memory 1114 and one or more processing units (or processor(s)) 1116. The processor(s) 1116 may be implemented as appropriate in hardware, computer-executable instructions, firmware, or combinations thereof. Computer-executable instruction or firmware implementations of the processor(s) 1116 may include computer-executable or machine-executable instructions written in any suitable programming language to perform the various functions described. The user device 1102 may also include geo-location devices (e.g., a global positioning system (GPS) device or the like) for providing and/or recording geographic location information associated with the user device 1102. In some examples, the wearable user device 1105 may also include geo-location devices for providing and/or recording geographic location information associated with wearable user device 1105.

The memory 1114 may store program instructions that are loadable and executable on the processor(s) 1116, as well as data generated during the execution of these programs. Depending on the configuration and type of the user device 1102, the memory 1114 may be volatile (such as random access memory (RAM)) and/or non-volatile (such as read-only memory (ROM), flash memory, etc.). The user device 1102 may also include additional removable storage and/or non-removable storage 1126 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1114 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 1114 and the additional storage 1126, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 1114 and the additional storage 1126 are both examples of non-transitory computer storage media. Additional types of computer storage media that may be present in the user devices 102, 104, 106, 146, 148 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 1102. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 1102 may also contain communications connection(s) 1128 that allow the user device 1102 to communicate with a data store, another computing device or server, user terminals, and/or other devices via the networks 1108, 1106. The user device 1102 may also include I/O device(s) 1130, such as a keyboard, a mouse, a pen, a voice input device, a touch input device, a display, an operating system 1132 and/or one or more application programs or services for implementing the features disclosed herein including a health application 1110(1). In some examples, the health application 1110(1) may be configured to implement the features described herein. As described in detail with reference to later figures, the wearable user device 1105 may include a memory that includes a similar health application 1110(2), which may be accessible by one or more processors of the wearable user device 1105. The service provider computer 1104 may also include a memory 1142 that includes a health application 1110(3). In this manner, the techniques described herein may be implemented by any one, or a combination of more than one, of the computing devices (e.g., the wearable user device 1105, the user device 1102, or the service provider computer 1104).

The service provider computers 1104 may also be any type of computing device such as, but not limited to, a mobile phone, a smartphone, a PDA, a laptop computer, a desktop computer, a thin-client device, a tablet computer, a wearable device, a server computer, a virtual machine instance, etc. In some examples, the service provider computers 1104 may be in communication with the user device 1102 and/or the wearable user device 1105 via the networks 1108, 1106, or via other network connections.

In one illustrative configuration, the service provider computers 1104 may include at least one memory 1142 and one or more processing units (or processor(s)) 1144. The processor(s) 1144 may be implemented as appropriate in hardware, computer-executable instructions, firmware, or combinations thereof. Computer-executable instruction or firmware implementations of the processor(s) 1144 may include computer-executable or machine-executable instructions written in any suitable programming language to perform the various functions described.

The memory 1142 may store program instructions that are loadable and executable on the processor(s) 1144, as well as data generated during the execution of these programs. Depending on the configuration and type of service provider computer 1104, the memory 1142 may be volatile (such as RAM) and/or non-volatile (such as ROM, flash memory, etc.). The service provider computer 1104 may also include additional removable storage and/or non-removable storage 1146 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1142 may include multiple different types of memory, such as SRAM, DRAM, or ROM. While the volatile memory described herein may be referred to as RAM, any volatile memory that would not maintain data stored therein once unplugged from a host and/or power would be appropriate. The memory 1142 and the additional storage 1146, both removable and non-removable, are both additional examples of non-transitory computer-readable storage media.

The service provider computer 1104 may also contain communications connection(s) 1148 that allow the service provider computer 1104 to communicate with a data store, another computing device or server, user terminals and/or other devices via the networks 1108, 1106. The service provider computer 1104 may also include I/O device(s) 1150, such as a keyboard, a mouse, a pen, a voice input device, a touch input device, a display, speakers, a printer, etc.

Turning to the contents of the memory 1142 in more detail, the memory 1142 may include an operating system 1152 and/or one or more application programs or services for implementing the features disclosed herein including the health application 1110(3).

Figure 12:
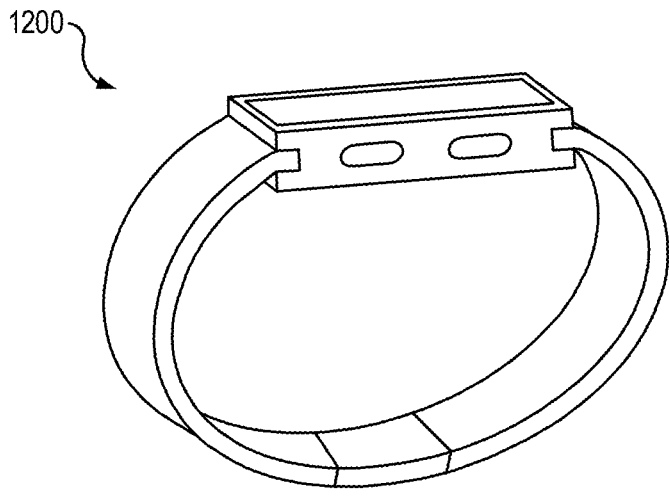
FIG. 12 illustrates an electronic device for implementing techniques relating to conducting sharing of health data updates among user devices and identifying changes in health data, according to at least one example.

Examples described herein may take the form of, be incorporated in, or operate with a suitable wearable electronic device. One example of such a device is shown in FIG. 12 and takes the form of a wearable mechanism 1200. As shown, the mechanism 1200 may be worn on a user's wrist and secured thereto by a band. The mechanism 1200 may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gathering data from one or more sensors that may be used to initiate, control, or modify operations of the device; determining a location of a touch on a surface of the device and/or an amount of force exerted on the device, and using either or both as input; accepting voice input to control one or more functions; accepting tactile input to control one or more functions; and so on.

Alternative examples of suitable electronic devices include a phone; a tablet computing device; a portable media player; and so on. Still other suitable electronic devices may include laptop/notebook computers, personal digital assistants, touch screens, input-sensitive pads or surfaces, and so on.

In some examples the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some examples, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such examples the band may include electrical interconnections that permit the two devices to transmit signals to one another and thereby interact with one another.

In many examples, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some examples.

The device may also include one or more touch sensors to determine a location of a touch on the cover glass. A touch sensor may be incorporated into or on the display stack in order to determine a location of a touch. The touch sensor may be self-capacitive in certain examples, mutual-capacitive in others, or a combination thereof.

Similarly, the device may include a force sensor to determine an amount of force applied to the cover glass. The force sensor may be a capacitive sensor in some examples and a strain sensor in other examples. In either example, the force sensor is generally transparent and made from transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one example the force sensor may take the form of a gasket extending beneath the periphery of the display. The gasket may be segmented or unitary, depending on the example.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative examples the haptic actuator may be rotary or any other type). A speaker may provide auditory components of an alert and the aforementioned display may provide visual alert components. In some examples a dedicated light, display, or other visual output component may be used as part of an alert.

The auditory, haptic, and/or visual components of the alert may be synchronized to provide an overall experience to a user. One or more components may be delayed relative to other components to create a desired synchronization among them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output, but at a weak or even subliminal level, thereby priming the wearer to receive the auditory output.

FIG. 13 depicts an example schematic diagram of an electronic device 1300. The electronic device 1300 is an example of the wearable user device 1105 and/or the user device 1102 (and other user devices described herein). As shown in FIG. 13, the device 1300 includes one or more processing units 1302 that are configured to access a memory 1304 having instructions stored thereon.

Memories 1304, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 1304 is an example of non-transitory computer storage media. Additional types of computer storage media that may be present in the user devices 102, 104, 106, 146, 148 may include, but are not limited to, phase-change RAM (PRAM), SRAM, DRAM, RAM, ROM, EEPROM, flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 1300. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The instructions or computer programs may be configured to perform one or more of the operations or functions described with respect to the device 1300 (e.g., the health application 710(2)). For example, the instructions may be configured to control or coordinate the operation of the various components of the device. Such components include, but are not limited to, display 1306, one or more input/output components 1308, one or more communication channels 1310, one or more sensors 1312, a speaker 1314, microphone 1316, a battery 1318, wireless power 1320, bio sensors 1322, and/or one or more haptic feedback devices 1324. In some examples the speaker and microphone may be combined into a single unit and/or may share a common port through a housing of the device.

The processing units 1302 of FIG. 13 may be implemented as any electronic device capable of processing, receiving, or transmitting data or instructions. For example, the processing units 1302 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

As shown in FIG. 13, the device 1300 may also include one or more acoustic elements, including a speaker 1314 and/or a microphone 1316. The speaker 1314 may include drive electronics or circuitry and may be configured to produce an audible sound or acoustic signal in response to a command or input. Similarly, the microphone 1316 may also include drive electronics or circuitry and is configured to receive an audible sound or acoustic signal in response to a command or input. The speaker 1314 and the microphone 1316 may be acoustically coupled to a port or opening in the case that allows acoustic energy to pass, but may prevent the ingress of liquid and other debris.

Figure 14:
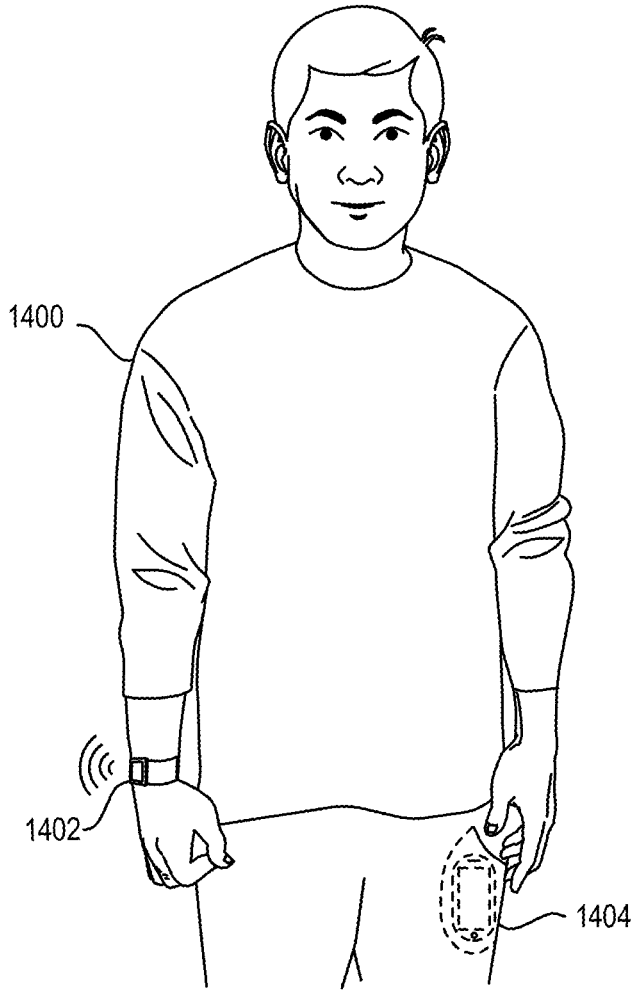
FIG. 14 illustrates a simplified diagram including example electronic devices for implementing techniques relating to conducting sharing of health data updates among user devices and identifying changes in health data, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 14 depicts a user 1400 wearing a first electronic device 1402 with a second electronic device 1404 in his pocket. Data may be wirelessly transmitted between the electronic devices 1402, 1404, thereby permitting the user 1400 to receive, view, and interact with data from the second device 1404 by means of the first electronic device 1402. Thus, the user 1400 may have access to part or all of the second device's functionality through the first electronic device 1402 without actually needing to interact directly with the second device 1404. In some examples, the second electronic device 1404 may be an example of the user device 1202. The first electronic device 1402 may be an example of the wearable user device 1205.

Further, the electronic devices 1402, 1404 may cooperate not only to share data, but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access, and the like between the two and ultimately to a user. As one non-limiting example, the electronic device 1402 may be unable to place or receive telephone calls while the second device 1404 may be able to do so. A user may nonetheless make and/or receive calls through the first device 1402, which may employ the second device 1404 to actually place or accept a call.

As another non-limiting example, an electronic device 1402 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain examples may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health data to be provided to a user. In some examples, the sensed biometric data may be used, in part, to determine the historic, current, and/or predicted activity data of the user.

Certain examples may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems may also be used (e.g., near field magnetic resonance and radio frequency). Alternatively, the device may also employ wired charging through electrodes.

In certain examples, the device may include a rotary input, which may take the form of a crown with a stem. The crown and stem may be rotated to provide the rotary input. Rotation of the stem and/or crown may be sensed optically, electrically, magnetically, or mechanically. Further, in some examples the crown and stem may also move laterally, thereby providing a second type of input to the device.

The electronic device may likewise include one or more buttons. The button(s) may be depressed to provide yet another input to the device. In various examples, the button may be a dome switch, rocker switch, electrical contact, magnetic switch, and so on. In some examples the button may be waterproof or otherwise sealed against the environment.

Various examples may include or otherwise incorporate one or more motion sensors. A motion sensor may detect motion of the device and provide, modify, cease, or otherwise affect a state, output, or input of the device or associated applications based at least in part on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some examples may use a GPS sensor to facilitate or enable location and/or navigation assistance.

Certain examples may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain examples of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Illustrative methods and systems for managing user device connections are described above. Some or all of these systems and methods may, but need not, be implemented at least partially by architectures such as those shown at least in FIGS. 1-14. While many of the examples are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

In the following, further examples are described to facilitate the understanding of the present disclosure.

Example 1. In this example, there is provided a computer-implemented method, comprising:

receiving, at a first user device associated with a user profile, a health database from a service provider, the health database associated with the user profile, the service provider configured to store the health database;

receiving, at the first user device, first health information associated with the user profile and collected, at least in part, by the first user device;

generating, at the first user device, a first health sync object based on the first health information, the first health sync object including a first sync identity that includes a first hardware identifier indicative of the first user device and a first database identifier indicative of the health database;

determining, at the first user device, to transmit the first health sync object to the service provider based on the first user device having responsibility to transmit health sync objects with the first sync identity to the service provider; and transmitting, to the service provider, the first health sync object.

Example 2. In this example, there is provided a method of any of the preceding or subsequent examples, further including: receiving a second health sync object, the second health sync object including a second sync identity that includes a second hardware identifier indicative of a second user device and a first database identifier indicative of the health database.

Example 3. In this example, there is provided a method of any of the preceding or subsequent examples, further including: determining, at the first user device, to not transmit the second health sync object to the service provider based on the first user device not having responsibility to transmit health sync objects with the second sync identity to the service provider.

Example 4. In this example, there is provided a method of any of the preceding or subsequent examples, further including:

determining, at the first user device, to transmit the second health sync object to the service provider based on the first user device having responsibility to transmit health sync objects with the second sync identity to the service provider; and transmitting, to the service provider, the second health sync object.

Example 5. In this example, there is provided a method of any of the preceding or subsequent examples, wherein the second sync identity is associated with a secondary device, wherein the method further comprises: receiving, at the first user device, an indication that the secondary device has not transmitted the first health sync object to the health database in accordance with a timing criteria.

Example 6. In this example, there is provided a method of any of the preceding or subsequent examples, wherein the second sync identity is associated with a second user device, wherein the second user device is no longer active.

Example 7. In this example, there is provided a method of any of the preceding or subsequent examples, wherein the second health sync object is received from the service provider, wherein the service provider is configured to transmit the second health sync object to the first user device based on determining that the second sync identity associated with the second health sync object is different from the first sync identity associated with the first user device.

Example 8. In this example, there is provided a first user device, including:

a memory configured to store computer-executable instructions; and one or more processors in communication with the memory and configured to access the memory and execute the computer-executable instructions to:

receive a health database from a service provider, the health database associated with a user profile, the first device associated with the user profile, the service provider configured to store the health database;

receive first health information associated with the user profile and collected, at least in part, by the first user device;

generate a first health sync object based on the first health information, the first health sync object including a first sync identity that includes a first hardware identifier indicative of the first user device and a first database identifier indicative of the health database;

determine to transmit the first health sync object to the service provider based on the first user device having responsibility to transmit health sync objects with the first sync identity to the service provider; and transmit the first health sync object.

Example 9. In this example, there is provided a first user device of any of the preceding or subsequent examples, wherein the one or more processors is further configured to access the memory and execute the computer-executable instructions to: receive a second health sync object, the second health sync object including a second sync identity that includes a second hardware identifier indicative of a second user device and a first database identifier indicative of the health database.

Example 10. In this example, there is provided a first user device of any of the preceding or subsequent examples, wherein the one or more processors is further configured to access the memory and execute the computer-executable instructions to: determine to not transmit the second health sync object to the service provider based on the first user device not having responsibility to transmit health sync objects with the second sync identity to the service provider.

Example 11. In this example, there is provided a first user device of any of the preceding or subsequent examples, wherein the one or more processors is further configured to access the memory and execute the computer-executable instructions to:

determine to transmit the second health sync object to the service provider based on the first user device having responsibility to transmit health sync objects with the second sync identity to the service provider; and transmit, to the service provider, the second health sync object.

Example 12. In this example, there is provided a first user device of any of the preceding or subsequent examples, wherein the second sync identity is associated with a secondary device, wherein the one or more processors is further configured to access the memory and execute the computer-executable instructions to: receive an indication that the secondary device has not transmitted the first health sync object to the health database in accordance with a timing criteria.

Example 13. In this example, there is provided a first user device of any of the preceding or subsequent examples, wherein the second sync identity is associated with a second user device, wherein the second user device is no longer active.

Example 14. In this example, there is provided one or more non-transitory computer-readable media comprising computer-executable instructions that, when executed by one or more processors on a first device, cause the one or more processors to perform operations including:

receiving, at a first user device associated with a user profile, a health database from a service provider, the health database associated with the user profile, the service provider configured to store the health database;

receiving, at the first user device, first health information associated with the user profile and collected, at least in part, by the first user device;

generating, at the first user device, a first health sync object based on the first health information, the first health sync object including a first sync identity that includes a first hardware identifier indicative of the first user device and a first database identifier indicative of the health database;

determining, at the first user device, to transmit the first health sync object to the service provider based on the first user device having responsibility to transmit health sync objects with the first sync identity to the service provider; and transmitting, to the service provider, the first health sync object.

Example 15. In this example, there is provided one or more non-transitory computer-readable media of any of the preceding or subsequent examples, wherein the operations further comprise receiving a second health sync object, the second health sync object including a second sync identity that includes a second hardware identifier indicative of a second user device and a first database identifier indicative of the health database.

Example 16. In this example, there is provided one or more non-transitory computer-readable media of any of the preceding or subsequent examples, wherein the operations further comprise determining, at the first user device, to not transmit the second health sync object to the service provider based on the first user device not having responsibility to transmit health sync objects with the second sync identity to the service provider.

Example 17. In this example, there is provided one or more non-transitory computer-readable media of any of the preceding or subsequent examples, wherein the operations further comprise:

determining, at the first user device, to transmit the second health sync object to the service provider based on the first user device having responsibility to transmit health sync objects with the second sync identity to the service provider; and transmitting, to the service provider, the second health sync object.

Example 18. In this example, there is provided one or more non-transitory computer-readable media of any of the preceding or subsequent examples, wherein the second sync identity is associated with a secondary device, wherein the operations further comprise:

receiving, at the first user device, an indication that the secondary device has not transmitted the first health sync object to the health database in accordance with a timing criteria.

Example 19. In this example, there is provided one or more non-transitory computer-readable media of any of the preceding or subsequent examples, wherein the second sync identity is associated with a second user device, wherein the second user device is no longer active.

Example 20. In this example, there is provided one or more non-transitory computer-readable media of any of the preceding or subsequent examples, wherein the service provider is configured to transmit the second health sync object to the first user device based on determining that the second sync identity associated with the second health sync object is different from the first sync identity associated with the first user device.

Example 20. In this example, there is provided a computer-implemented method, including:

transmitting, to a first user device, a health database from a service provider, the health database associated with a user profile, the service provider configured to store the health database;

receiving, at the service provider from the first user device, a first health sync object, wherein the first health sync object is based on first health information collected, at least in part, at the first user device, the first health sync object including a first sync identity that includes a first hardware identifier indicative of the first user device and a first database identifier indicative of the health database;

identifying, at the service provider, a second user device to receive the first health sync object, wherein the second user device is associated with the health database;

determining that the first sync identity is different from a second sync identity associated with the second user device; and based on determining that the first sync identity is different from the second sync identity, transmitting, to the second user device, the first health sync object.

Example 21. In this example, there is provided a computer-implemented method of any of the preceding or subsequent examples, further comprising:

receiving, at the service provider, a third health sync object, wherein the third health sync object is associated with a third sync identity, the third sync identity associated with a third user device, wherein the third user device is no longer active; and determining, at the service provider, to not transmit the third health sync object to the first user device based on the first user device having responsibility to transmit health sync objects with the third sync identity to the service provider.

Example 22. In this example, there is provided a computer-implemented method of any of the preceding or subsequent examples, further comprising:

receiving, at the service provider from the second user device, a second health sync object, the second health sync object including a second sync identity that includes a second hardware identifier indicative of the second user device and a first database identifier indicative of the health database;

identifying, at the service provider, the first user device to receive the second health sync object;

determining that the second sync identity is different from the first sync identity; and based on determining that the second sync identity is different from the first sync identity, transmitting, to the first user device, the second health sync object.

Example 24. In this example, there is provided a computer-implemented method of any of the preceding or subsequent examples, further comprising:

identifying, at the service provider, a third user device, wherein the third user device is associated with the health database, wherein the third user device is a secondary device;

determining, at the service provider, to not transmit the first health sync object to the third user device based on the third user device being a secondary device.

Example 25. In this example, there is provided a computer-implemented method of any of the preceding or subsequent examples, further comprising:

identifying, at the service provider, a third user device, wherein the third user device is associated with the health database, wherein the third user device is a secondary device associated with the first user device;

determining, at the service provider, to not transmit the first health sync object to the third user device based on the third user device being a secondary device associated with the first user device.

Example 26. In this example, there is provided a computer-implemented method of any of the preceding or subsequent examples, further comprising:

identifying, at the service provider, a third user device, wherein the third user device is associated with the health database, wherein the third user device is a primary device associated with the first user device;

determining, at the service provider, to not transmit the first health sync object to the third user device based on the third user device being a primary device associated with the first user device.

Example 27. In this example, there is provided a computer-implemented method of any of the preceding or subsequent examples, wherein transmitting the first health sync object to the second user device is further based on determining that the second user device does not have responsibility to transmit health sync objects with the first sync identity to the service provider.

Example 28. In this example, there is provided a computer system, including:

a memory configured to store computer-executable instructions; and one or more processors in communication with the memory and configured to access the memory and execute the computer-executable instructions to:

transmit, to a first user device, a health database from a service provider, the health database associated with a user profile, the service provider configured to store the health database;

receive, from the first user device, a first health sync object, wherein the first health sync object is based on first health information collected, at least in part, at the first user device, the first health sync object including a first sync identity that includes a first hardware identifier indicative of the first user device and a first database identifier indicative of the health database;

identify a second user device to receive the first health sync object, wherein the second user device is associated with the health database;

determine that the first sync identity is different from a second sync identity associated with the second user device; and based on determining that the first sync identity is different from the second sync identity, transmit, to the second user device, the first health sync object.

Example 28. In this example, there is provided a computer system of any of the preceding or subsequent examples, wherein the one or more processors is further configured to access the memory and execute the computer-executable instructions to:

receive a third health sync object, wherein the third health sync object is associated with a third sync identity, the third sync identity associated with a third user device, wherein the third user device is no longer active; and determine to not transmit the third health sync object to the first user device based on the first user device having responsibility to transmit health sync objects with the third sync identity to the service provider.

Example 29. In this example, there is provided a computer system of any of the preceding or subsequent examples, wherein the one or more processors is further configured to access the memory and execute the computer-executable instructions to:

receive, from the second user device, a second health sync object, the second health sync object including a second sync identity that includes a second hardware identifier indicative of the second user device and a first database identifier indicative of the health database;

identify the first user device to receive the second health sync object;

determine that the second sync identity is different from the first sync identity; and based on determining that the second sync identity is different from the first sync identity, transmit, to the first user device, the second health sync object.

Example 30. In this example, there is provided a computer system of any of the preceding or subsequent examples, wherein the one or more processors is further configured to access the memory and execute the computer-executable instructions to:

identify, a third user device, wherein the third user device is associated with the health database, wherein the third user device is a secondary device;

determining, to not transmit the first health sync object to the third user device based on the third user device being a secondary device.

Example 31. In this example, there is provided a computer system of any of the preceding or subsequent examples, wherein the first user device is a primary device, wherein the one or more processors is further configured to access the memory and execute the computer-executable instructions to:

identify a third user device, wherein the third user device is associated with the health database, wherein the third user device is a secondary device associated with the first user device;

determine to not transmit the first health sync object to the third user device based on the third user device being a secondary device associated with the first user device.

Example 31. In this example, there is provided a computer system of any of the preceding or subsequent examples, wherein the first user device is a secondary device, wherein the one or more processors is further configured to access the memory and execute the computer-executable instructions to:

identify a third user device, wherein the third user device is associated with the health database, wherein the third user device is a primary device associated with the first user device;

determine to not transmit the first health sync object to the third user device based on the third user device being a primary device associated with the first user device.

Example 34. In this example, there is provided a computer system of any of the preceding or subsequent examples, wherein transmitting the first health sync object to the second user device is further based on determining that the second user device does not have responsibility to transmit health sync objects with the first sync identity to the service provider.

Example 35. In this example, there is provided one or more non-transitory computer-readable media comprising computer-executable instructions that, when executed by one or more processors of a first device, cause the one or more processors to perform operations comprising: transmitting, to a first user device, a health database from a service provider, the health database associated with a user profile, the service provider configured to store the health database;

receiving, at the service provider from a first user device, a first health sync object, wherein the first health sync object is based on first health information collected, at least in part, at the first user device, the first health sync object including a first sync identity that includes a first hardware identifier indicative of the first user device and a first database identifier indicative of the health database;

identifying, at the service provider, a second user device to receive the first health sync object, wherein the second user device is associated with the health database;

determining that the first sync identity is different from a second sync identity associated with the second user device; and based on determining that the first sync identity is different from the second sync identity, transmitting, to the second user device, the first health sync object.

Example 36. In this example, there is provided one or more non-transitory computer-readable media of any of the preceding or subsequent examples, wherein the operations further comprise:

receiving, at the service provider, a third health sync object, wherein the third health sync object is associated with a third sync identity, the third sync identity associated with a third user device, wherein the third user device is no longer active; and determining, at the service provider, to not transmit the third health sync object to the first user device based on the first user device having responsibility to transmit health sync objects with the third sync identity to the service provider.

Example 37. In this example, there is provided one or more non-transitory computer-readable media of any of the preceding or subsequent examples, wherein the operations further comprise:

receiving, at the service provider from the second user device, a second health sync object, the second health sync object including a second sync identity that includes a second hardware identifier indicative of the second user device and a first database identifier indicative of the health database;

identifying, at the service provider, the first user device to receive the second health sync object;

determining that the second sync identity is different from the first sync identity; and based on determining that the second sync identity is different from the first sync identity, transmitting, to the first user device, the second health sync object.

Example 38. In this example, there is provided one or more non-transitory computer-readable media of any of the preceding or subsequent examples, wherein the operations further comprise:

identifying, at the service provider, a third user device, wherein the third user device is associated with the health database, wherein the third user device is a secondary device;

determining, at the service provider, to not transmit the first health sync object to the third user device based on the third user device being a secondary device.

Example 39. In this example, there is provided one or more non-transitory computer-readable media of any of the preceding or subsequent examples, wherein the operations further comprise:

identifying, at the service provider, a third user device, wherein the third user device is associated with the health database, wherein the third user device is a secondary device associated with the first user device;

determining, at the service provider, to not transmit the first health sync object to the third user device based on the third user device being a secondary device associated with the first user device.

Example 40. In this example, there is provided one or more non-transitory computer-readable media of any of the preceding or subsequent examples, wherein the first user device is a secondary device, wherein the operations further comprise:

identifying, at the service provider, a third user device, wherein the third user device is associated with the health database, wherein the third user device is a primary device associated with the first user device;

determining, at the service provider, to not transmit the first health sync object to the third user device based on the third user device being a primary device associated with the first user device.

Example 41. In this example, there is provided a computer-implemented method, including:

receiving, at a primary device, a first health sync object based on first health information associated with a user profile, the user profile associated with a health database, a service provider configured to store the health database, the first health sync object including a first sync identity, that includes a first hardware identifier indicative of the secondary device and a first database identifier indicative of the health database, the secondary device configured to transmit the first health sync object to the service provider;

receiving, at the primary device, an indication that the secondary device has not transmitted the first health sync object to the service provider in accordance with a timing criteria; and transmitting, to the service provider, the first health sync object.

Example 42. In this example, there is provided a computer-implemented method of any of the preceding or subsequent examples, further comprising transmitting, to the secondary device, a request for an indication whether the secondary device has transmitted the first health sync object to the service provider.

Example 43. In this example, there is provided a computer-implemented method of any of the preceding or subsequent examples, wherein the secondary device is configured to have a store of health information limited to health information associated with the health database from a last time period.

Example 44. In this example, there is provided a computer-implemented method of any of the preceding or subsequent examples, wherein the secondary device is configured to delete health information associated with a time outside the last time period.

Example 45. In this example, there is provided a computer-implemented method of any of the preceding or subsequent examples, further comprising:

receiving, at the primary device, a second health information associated with the user profile;

generating, at the primary device, second health sync object based on the second health information, the second health sync object including a second sync identity that includes a second hardware identifier indicative of the primary device and the first database identifier; and transmitting, to the service provider, the second health sync object.

Example 46. In this example, there is provided a computer-implemented method of any of the preceding or subsequent examples, wherein the primary device transmits and receives information from the secondary device over a short-range communication medium.

Example 47. In this example, there is provided a computer-implemented method of any of the preceding or subsequent examples, wherein the primary device has responsibility to transmit, to the service provider, health sync objects with the first sync identity and health sync objects with a second sync identity, the second sync identity associated with a third user device, wherein the third user device is no longer active.

Example 48. In this example, there is provided a computer-implemented method of any of the preceding or subsequent examples, wherein the primary device has responsibility to transmit, to the secondary device, health sync objects with sync identities other than the first sync identity.

Example 49. In this example, there is provided a primary device, including:

a memory configured to store computer-executable instructions; and one or more processors in communication with the memory and configured to access the memory and execute the computer-executable instructions to:

receive a first health sync object based on first health information associated with a user profile, the user profile associated with a health database, a service provider configured to store the health database, the first health sync object including a first sync identity, that includes a first hardware identifier indicative of the secondary device and a first database identifier indicative of the health database, the secondary device configured to transmit the first health sync object to the service provider;

receive an indication that the secondary device has not transmitted the first health sync object to the service provider in accordance with a timing criteria; and transmit, to the service provider, the first health sync object.

Example 50. In this example, there is provided a primary device of any of the preceding or subsequent examples, wherein the one or more processors is further configured to access the memory and execute the computer-executable instructions to:

transmit, to the secondary device, a request for an indication whether the secondary device has transmitted the first health sync object to the service provider.

Example 51. In this example, there is provided a primary device of any of the preceding or subsequent examples, wherein the secondary device is configured to have a store of health information limited to health information associated with the health database from a last time period, wherein the secondary device is configured to delete health information associated with a time outside the last time period.

Example 52. In this example, there is provided a primary device of any of the preceding or subsequent examples, wherein the one or more processors is further configured to access the memory and execute the computer-executable instructions to:

receive a second health information associated with the user profile;

generate second health sync object based on the second health information, the second health sync object including a second sync identity that includes a second hardware identifier indicative of the primary device and the first database identifier; and transmit, to the service provider, the second health sync object.

Example 53. In this example, there is provided a primary device of any of the preceding or subsequent examples, wherein the primary device has responsibility to transmit, to the service provider, health sync objects with the first sync identity and health sync objects with a second sync identity, the second sync identity associated with a third user device, wherein the third user device is no longer active.

Example 54. In this example, there is provided a primary device of any of the preceding or subsequent examples, wherein the primary device has responsibility to transmit, to the secondary device, health sync objects with sync identities other than the first sync identity.

Example 55. In this example, there is provided One or more non-transitory computer-readable media comprising computer-executable instructions that, when executed by one or more processors on a first device, cause the one or more processors to perform operations comprising:

receiving, at a primary device, a first health sync object based on first health information associated with a user profile, the user profile associated with a health database, a service provider configured to store the health database, the first health sync object including a first sync identity, that includes a first hardware identifier indicative of the secondary device and a first database identifier indicative of the health database, the secondary device configured to transmit the first health sync object to the service provider;

receiving, at the primary device, an indication that the secondary device has not transmitted the first health sync object to the service provider in accordance with a timing criteria; and transmitting, to the service provider, the first health sync object.

Example 56. In this example, there is provided one or more non-transitory computer-readable media of any of the preceding or subsequent examples, wherein the operations further comprise transmitting, to the secondary device, a request for an indication whether the secondary device has transmitted the first health sync object to the service provider.

Example 57. In this example, there is provided one or more non-transitory computer-readable media of any of the preceding or subsequent examples, wherein the secondary device is configured to have a store of health information limited to health information associated with the health database from a last time period, wherein the secondary device is configured to delete health information associated with a time outside the last time period.

Example 58. In this example, there is provided one or more non-transitory computer-readable media of any of the preceding or subsequent examples, wherein the operations further comprise:

receiving, at the primary device, a second health information associated with the user profile;

generating, at the primary device, second health sync object based on the second health information, the second health sync object including a second sync identity that includes a second hardware identifier indicative of the primary device and the first database identifier; and transmitting, to the service provider, the second health sync object.

Example 59. In this example, there is provided one or more non-transitory computer-readable media of any of the preceding or subsequent examples, wherein the primary device has responsibility to transmit, to the service provider, health sync objects with the first sync identity and health sync objects with a second sync identity, the second sync identity associated with a third user device, wherein the third user device is no longer active.

Example 60. In this example, there is provided one or more non-transitory computer-readable media of any of the preceding or subsequent examples, wherein the primary device has responsibility to transmit, to the secondary device, health sync objects with sync identities other than the first sync identity.

Example 61. In this example, there is provided a computer-implemented method, comprising:

receiving, at a secondary device, first health information associated with a user profile, the user profile associated with a health database that is stored by a service provider;

generating, at the secondary device, a first health sync object based on the first health information, the first health sync object including a first sync identity that includes a first hardware identifier indicative of the secondary device and a first database identifier indicative of the health database, the secondary device configured to transmit the first health sync object to the service provider;

transmitting, to a primary device, the first health sync object;

determining, in accordance with a timing criteria, that the secondary device has not transmitted the first health sync object to the service provider; and transmitting, to the primary device, an indication that the secondary device has not transmitted the first health sync object to the service provider, wherein the indication is configured to cause the primary device to transmit the first health sync object to the service provider.

Example 62. In this example, there is provided a computer-implemented method of any of the preceding or subsequent examples, further comprising receiving, from the primary device, a request for an indication whether the secondary device has transmitted the first health sync object to the service provider.

Example 63. In this example, there is provided a computer-implemented method of any of the preceding or subsequent examples, further comprising:

receiving, at a secondary device, second health information associated with the user profile;

generating, at the secondary device, a second health sync object based on the second health information, the second health sync object including the first sync identity; and transmitting, to the service provider, the second health sync object.

Example 64. In this example, there is provided a computer-implemented method of any of the preceding or subsequent examples, wherein the secondary device has a store of health information limited to health information associated with the health database from a last time period.

Example 65. In this example, there is provided a computer-implemented method of any of the preceding or subsequent examples, wherein the secondary device deletes health information associated with a time outside the last time period.

Example 66. In this example, there is provided a computer-implemented method of any of the preceding or subsequent examples, wherein the secondary device transmits and receives information from the primary device over a short-range communication medium.

Example 67. In this example, there is provided a computer-implemented method of any of the preceding or subsequent examples, wherein the primary device is configured to generate a second health sync object including a second sync identity that includes a second hardware identifier indicative of the primary device and the first database identifier, wherein the primary device is configured to transmit the second health sync object to the service provider.

Example 68. In this example, there is provided a computer-implemented method of any of the preceding or subsequent examples, wherein the primary device is configured to have responsibility to transmit health sync objects with the first sync identity and health sync objects with the second sync identity to the service provider.

Example 62. In this example, there is provided a secondary device, comprising:

a memory configured to store computer-executable instructions; and one or more processors in communication with the memory and configured to access the memory and execute the computer-executable instructions to:

receive first health information associated with a user profile, the user profile associated with a health database that is stored by a service provider;

generate a first health sync object based on the first health information, the first health sync object including a first sync identity that includes a first hardware identifier indicative of the secondary device and a first database identifier indicative of the health database, the secondary device configured to transmit the first health sync object to the service provider;

transmit, to a primary device, the first health sync object;

determine, in accordance with a timing criteria, that the secondary device has not transmitted the first health sync object to the service provider; and transmit, to the primary device, an indication that the secondary device has not transmitted the first health sync object to the service provider, wherein the indication is configured to cause the primary device to transmit the first health sync object to the service provider.

Example 70. In this example, there is provided a secondary device of any of the preceding or subsequent examples, wherein the one or more processors is further configured to access the memory and execute the computer-executable instructions to: receiving, from the primary device, a request for an indication whether the secondary device has transmitted the first health sync object to the service provider.

Example 71. In this example, there is provided a secondary device of any of the preceding or subsequent examples, wherein the one or more processors is further configured to access the memory and execute the computer-executable instructions to:

receive second health information associated with the user profile;

generate a second health sync object based on the second health information, the second health sync object including the first sync identity; and transmit, to the service provider, the second health sync object.

Example 72. In this example, there is provided a secondary device of any of the preceding or subsequent examples, wherein the secondary device has a store of health information limited to health information associated with the health database from a last time period.

Example 73. In this example, there is provided a secondary device of any of the preceding or subsequent examples, wherein the secondary device transmits and receives information from the primary device over a short-range communication medium.

Example 74. In this example, there is provided a secondary device of any of the preceding or subsequent examples, wherein the primary device is configured to generate a second health sync object including a second sync identity that includes a second hardware identifier indicative of the primary device and the first database identifier, wherein the primary device is configured to transmit the second health sync object to the service provider, wherein the primary device is configured to have responsibility to transmit health sync objects with the first sync identity and health sync objects with the second sync identity to the service provider.

Example 75. In this example, there is provided one or more non-transitory computer-readable media comprising computer-executable instructions that, when executed by one or more processors on a first device, cause the one or more processors to perform operations comprising: receiving, at a secondary device, first health information associated with a user profile, the user profile associated with a health database that is stored by a service provider; generating, at the secondary device, a first health sync object based on the first health information, the first health sync object including a first sync identity that includes a first hardware identifier indicative of the secondary device and a first database identifier indicative of the health database, the secondary device configured to transmit the first health sync object to the service provider;

transmitting, to a primary device, the first health sync object;

determining, in accordance with a timing criteria, that the secondary device has not transmitted the first health sync object to the service provider; and transmitting, to the primary device, an indication that the secondary device has not transmitted the first health sync object to the service provider, wherein the indication is configured to cause the primary device to transmit the first health sync object to the service provider.

Example 76. In this example, there is provided one or more non-transitory computer-readable media of any of the preceding or subsequent examples, wherein the operations further comprise receiving, from the primary device, a request for an indication whether the secondary device has transmitted the first health sync object to the service provider.

Example 77. In this example, there is provided one or more non-transitory computer-readable media of any of the preceding or subsequent examples, wherein the operations further comprise:

receiving, at a secondary device, second health information associated with the user profile;

generating, at the secondary device, a second health sync object based on the second health information, the second health sync object including the first sync identity; and transmitting, to the service provider, the second health sync object.

Example 78. In this example, there is provided one or more non-transitory computer-readable media of any of the preceding or subsequent examples, wherein the secondary device has a store of health information limited to health information associated with the health database from a last time period.

Example 79. In this example, there is provided one or more non-transitory computer-readable media of any of the preceding or subsequent examples, wherein the secondary device deletes health information associated with a time outside the last time period.

Example 80. In this example, there is provided one or more non-transitory computer-readable media of any of the preceding or subsequent examples, wherein the primary device is configured to generate a second health sync object including a second sync identity that includes a second hardware identifier indicative of the primary device and the first database identifier, wherein the primary device is configured to transmit the second health sync object to the service provider, wherein the primary device is configured to have responsibility to transmit health sync objects with the first sync identity and health sync objects with the second sync identity to the service provider.

The various examples further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets)

or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is sharing health data updates between user devices, which may include storing some aspect of the data on a server. The present disclosure contemplates that in some instances, this gathered data may include personally identifiable information (PII) data that uniquely identifies or can be used to contact or locate a specific person. Such personal information data can include demographic data, location-based data, telephone numbers, email addresses, Twitter IDs, home addresses, data or records relating to a user's health or level of fitness (e.g., vital sign measurements, medication information, exercise information), date of birth, health record data, or any other identifying or personal or health information.

The present disclosure recognizes that the use of such personal information data, in the present technology, can be used to the benefit of users. For example, the personal information data can be used to provide a family member or friend a view of health data updates. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the U.S., collection of or access to certain health data may be governed by federal and/or state laws, such as the Health Insurance Portability and Accountability Act (HIPAA); whereas health data in other countries may be subject to other regulations and policies and should be handled accordingly. Hence, different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health-related applications, data de-identification can be used to protect a user's privacy. De-identification may be facilitated, when appropriate, by removing specific identifiers (e.g., date of birth), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. A computer-implemented method, comprising:

receiving, at a first user device associated with a user profile, a health database from a service provider, the health database associated with the user profile, the service provider configured to store the health database;

receiving, at the first user device, first health information associated with the user profile and collected, at least in part, by the first user device;

generating, at the first user device, a first health sync object based on the first health information, the first health sync object including a first sync identity that includes a first hardware identifier indicative of the first user device that generated the first health sync object and a first database identifier indicative of the health database;

determining, at the first user device, to transmit the first health sync object to the service provider based on the first user device being configured to transmit health sync objects with the first sync identity to the service provider and based on the first user device being configured to refrain from transmitting health sync objects with a different sync identity from the first sync identity to the service provider;

transmitting, to the service provider, the first health sync object;

receiving, at the first user device, a second health sync object, the second health sync object including a second sync identity that includes a second hardware identifier indicative of a second user device and the first database identifier indicative of the health database; and determining, at the first user device, to not transmit the second health sync object to the service provider based on the first user device not transmitting health sync objects with the second sync identity to the service provider.

2. The computer implemented method of claim 1, the method further comprising:

receiving, at the first user device, a third health sync object, the third health sync object including a third sync identity that includes a third hardware identifier indicative of a third user device and the first database identifier indicative of the health database, the first user device is further configured to transmit health sync objects with the third sync identity to the service provider;

determining, at the first user device, to transmit the third health sync object to the service provider based on the first user device transmitting health sync objects with the third sync identity to the service provider; and transmitting, to the service provider, the third health sync object.

3. The computer implemented method of claim 2, wherein the third sync identity is associated with a secondary device, wherein the method further comprises:

receiving, at the first user device, an indication that the secondary device has not transmitted the third health sync object to the health database in accordance with a timing criterion.

4. The computer-implemented method of claim 3, wherein determining to transmit the third health sync object to the service provider is based at least in part on the indication that the secondary device has not transmitted the third health sync object to the health database in accordance with the timing criterion.

5. The computer implemented method of claim 2, wherein the third sync identity is associated with the third user device, wherein the third user device is no longer active.

6. The computer implemented method of claim 1, the method further comprising receiving, at the first device, a third health sync object from the service provider, the third health sync object including a third sync identity that includes a third hardware identifier indicative of a third user device and the first database identifier indicative of the health database, wherein the service provider is configured to transmit the third health sync object to the first user device based on determining that the third sync identity associated with the third health sync object is different from the first sync identity associated with the first user device.

7. The computer implemented method of claim 1, wherein in the first health sync object comprises a discrete and fundamental unit of the first health information that can be synced between the first user device and at least one of the second user device or the service provider.

8. A first user device, comprising:

a memory configured to store computer-executable instructions; and one or more processors in communication with the memory and configured to access the memory and execute the computer-executable instructions to:

receive a health database from a service provider, the health database associated with a user profile, the first user device associated with the user profile, the service provider configured to store the health database;

receive first health information associated with the user profile and collected, at least in part, by the first user device;

generate, at the first user device, a first health sync object based on the first health information, the first health sync object including a first sync identity that includes a first hardware identifier indicative of the first user device that generated the first health sync object and a first database identifier indicative of the health database;

determine to transmit the first health sync object to the service provider based on the first user device being configured to transmit health sync objects with the first sync identity to the service provider and based on the first user device being configured to refrain from transmitting health sync objects with a different sync identity from the first sync identity to the service provider;

transmit the first health sync object;

receive a second health sync object, the second health sync object including a second sync identity that includes a second hardware identifier indicative of a second user device and the first database identifier indicative of the health database; and determine to not transmit the second health sync object to the service provider based on the first user device not transmitting health sync objects with the second sync identity to the service provider.

9. The first user device of claim 8, wherein the one or more processors is further configured to access the memory and execute the computer-executable instructions to:

receive a third health sync object, the third health sync object including a third sync identity that includes a third hardware identifier indicative of a third user device and the first database identifier indicative of the health database, the first user device is further configured to transmit health sync objects with the third sync identity to the service provider;

determine to transmit the third health sync object to the service provider based on the first user device transmitting health sync objects with the third sync identity to the service provider; and transmit the third health sync object.

10. The first user device of claim 9, wherein the third sync identity is associated with a secondary device, wherein the one or more processors is further configured to access the memory and execute the computer-executable instructions to:

receive an indication that the secondary device has not transmitted the third health sync object to the health database in accordance with a timing criterion.

11. The first user device of claim 10, wherein determining to transmit the third health sync object to the service provider is based at least in part on the indication that the secondary device has not transmitted the third health sync object to the health database in accordance with a timing criterion.

12. The first user device of claim 9, wherein the third sync identity is associated with the third user device, wherein the third user device is no longer active.

13. The first user device of claim 8, wherein in the first health sync object comprises a discrete and fundamental unit of the first health information that can be synced between the first user device and at least one of the second user device or the service provider.

14. One or more non-transitory computer-readable media comprising computer-executable instructions that, when executed by one or more processors on a first user device, cause the one or more processors to perform operations comprising:

receiving, at the first user device associated with a user profile, a health database from a service provider, the health database associated with the user profile, the service provider configured to store the health database;

receiving, at the first user device, first health information associated with the user profile and collected, at least in part, by the first user device;

generating, at the first user device, a first health sync object based on the first health information, the first health sync object including a first sync identity that includes a first hardware identifier indicative of the first user device that generated the first health sync object and a first database identifier indicative of the health database;

determining, at the first user device, to transmit the first health sync object to the service provider based on the first user device being configured to transmit health sync objects with the first sync identity to the service provider and based on the first user device being configured to refrain from transmitting health sync objects with a different sync identity from the first sync identity to the service provider;

transmitting, to the service provider, the first health sync object;

receiving, at the first user device, a second health sync object, the second health sync object including a second sync identity that includes a second hardware identifier indicative of a second user device and the first database identifier indicative of the health database; and determining, at the first user device, to not transmit the second health sync object to the service provider based on the first user device not transmitting health sync objects with the second sync identity to the service provider.

15. The one or more non-transitory computer-readable media of claim 14, wherein the operations further comprise:

receiving, at the first user device, a third health sync object, the third health sync object including a third sync identity that includes a third hardware identifier indicative of a third user device and the first database identifier indicative of the health database, the first user device is further configured to transmit health sync objects with the third sync identity to the service provider:

determining, at the first user device, to transmit the third health sync object to the service provider based on the first user device transmitting health sync objects with the third sync identity to the service provider; and transmitting, to the service provider, the third health sync object.

16. The one or more non-transitory computer-readable media of claim 15, wherein the third sync identity is associated with a secondary device, wherein the operations further comprise:

receiving, at the first user device, an indication that the secondary device has not transmitted the third health sync object to the health database in accordance with a timing criterion.

17. The one or more non-transitory computer-readable media of claim 16, wherein determining to transmit the third health sync object to the service provider is based at least in part on the indication that the secondary device has not transmitted the third health sync object to the health database in accordance with a timing criterion.

18. The one or more non-transitory computer-readable media of claim 15, wherein the third sync identity is associated with the third user device, wherein the third user device is no longer active.

19. The one or more non-transitory computer-readable media of claim 14, wherein the operations further comprise receiving, at the first device, a third health sync object from the service provider, the third health sync object including a third sync identity that includes a third hardware identifier indicative of a third user device and the first database identifier indicative of the health database, wherein the service provider is configured to transmit the third health sync object to the first user device based on determining that the third sync identity associated with the third health sync object is different from the first sync identity associated with the first user device.

20. The one or more non-transitory computer-readable media of claim 14, wherein in the first health sync object comprises a discrete and fundamental unit of the first health information that can be synced between the first user device and at least one of the second user device or the service provider.

* * * * *